United States Patent
Coughlin et al.

(10) Patent No.: US 7,494,998 B2
(45) Date of Patent: Feb. 24, 2009

(54) BENZISOXAZOLE PIPERAZINE COMPOUNDS AND METHODS OF USE THEREOF

(75) Inventors: Daniel Coughlin, Hackettstown, NJ (US); James F. White, Carlisle, MA (US); Kazumi Shiosaki, Wellesley, MA (US); David G. Hangauer, East Amherst, NY (US); Michael Solomon, Concord, MA (US); Dale M. Edgar, Wayland, MA (US)

(73) Assignee: Hypnion, Inc., Indianapolis, IN (US)

( * ) Notice: Subject to any disclaimer, the term of this patent is extended or adjusted under 35 U.S.C. 154(b) by 274 days.

(21) Appl. No.: 11/412,856

(22) Filed: Apr. 26, 2006

(65) Prior Publication Data

US 2007/0004752 A1 Jan. 4, 2007

Related U.S. Application Data

(60) Provisional application No. 60/675,202, filed on Apr. 26, 2005.

(51) Int. Cl.
*A61K 31/497* (2006.01)
*C07D 413/00* (2006.01)
*C07D 417/00* (2006.01)
*C07D 419/00* (2006.01)

(52) U.S. Cl. .................. 514/254.02; 544/368
(58) Field of Classification Search ............. 544/368; 514/254.02

See application file for complete search history.

(56) References Cited

U.S. PATENT DOCUMENTS

| | | | |
|---|---|---|---|
| 5,134,147 A | 7/1992 | Peglion et al. | 514/300 |
| 5,364,866 A | 11/1994 | Strupczewski et al. | 514/321 |
| 5,776,963 A | 7/1998 | Strupczewski et al. | 514/373 |
| 6,218,404 B1 | 4/2001 | Bigge et al. | 514/317 |
| 6,331,541 B1 | 12/2001 | Ko et al. | 514/237.2 |
| 6,605,623 B1 | 8/2003 | Ko et al. | 514/331 |
| 7,355,042 B2 | 4/2008 | Edgar et al. | 540/542 |

FOREIGN PATENT DOCUMENTS

| | | |
|---|---|---|
| EP | 0 428 437 A1 | 5/1991 |
| EP | 0 542 136 B1 | 5/1993 |
| WO | WO 94/27994 | 12/1994 |
| WO | WO 97/21439 | 6/1997 |
| WO | WO 97/49698 | 12/1997 |
| WO | WO 02/066446 A1 | 8/2002 |

OTHER PUBLICATIONS

Roizenblatt, S., et al., A Double-blind, Placebo-Controlled, Crossover Study of Sildenafil in Obstructive Sleep Apnea, Arch Intern Med., 166: 1763-1767 (2006).*
West, Anthony R., Solid State Chemistry and Its Applications, Wiley, New York, 1988, 358.*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
Hansen et al. *Eur. J. Med. Chem.*, 33:839-858 (1998).
International Search Report for PCT/US2006/016057, mailed Aug. 21, 2006.
Leopoldo et al., "Structure-affinity relationship study on N-(1,2,3,4-tetrahydronaphthalen-1-yl)-4-aryl-1-piperazinealkylamides, a new class of 5-hydroxytryptamine$_7$ receptor agents", *J. Med. Chem.*, 47:6616-6624 (2004).
International Search Report for PCT/US2006/016059, mailed Aug. 30, 2006.

* cited by examiner

*Primary Examiner*—James O Wilson
*Assistant Examiner*—Erich A Leeser
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention includes benzisoxazole piperazine compositions and methods of using them for modulating sleep.

6 Claims, No Drawings

BENZISOXAZOLE PIPERAZINE COMPOUNDS AND METHODS OF USE THEREOF

RELATED APPLICATIONS

This non-provisional patent application claims priority under 35 U.S.C. § 119(e) to U.S. Provisional Patent Application Ser. No. 60/675,202, filed Apr. 26, 2005 which is herein incorporated by reference in its entirety.

FIELD OF THE INVENTION

The invention relates to methods for treating sleep disorders and compositions useful in such methods.

BACKGROUND OF THE INVENTION

Difficulty falling asleep or remaining asleep is a significant medical issue that arises for a variety of reasons. Sometimes, these problems arise from endogenous conditions such as sleep apnea or insomnia. Other times, these problems arise from exogenous stresses such as the disruptive effect of shift work schedules and "jet lag." Whether caused by an endogenous or exogenous source, difficulty falling asleep or remaining asleep can result in problem sleepiness, which impairs the health, quality of life, and safety of those affected.

Existing pharmaceutical treatments for inducing sleep include sedatives or hypnotics such as benzodiazepine and barbiturate derivatives. These treatments have numerous drawbacks, including rebound insomnia, delayed onset of desired sedative effects, persistence of sedative effects after the desired sleep period, and side effects due to nonspecific activity such as psychomotor and memory deficits, myorelaxation, and disturbed sleep architecture, including REM sleep inhibition. Additionally, sedatives and hypnotics can be habit forming, can lose their effectiveness after extended use, and may be metabolized more slowly by some people.

Consequently, physicians often recommend or prescribe antihistamines as a milder treatment for sleep disorders when hypnotics are less appropriate. However, many antihistamines suffer from a number of side effects. These side effects include prolongation of the QT interval in a subject's electrocardiogram, as well as central nervous system (CNS) side effects such as decreased muscle tone and drooping eyelids. Finally, such compounds can bind to muscarinic receptors, which leads to anti-cholinergic side effects such as blurred vision, dry mouth, constipation, urinary problems, dizziness and anxiety.

As a result, there is a need for sleep-promoting treatments with reduced side effects. Additionally, while known sleep-inducing compounds are effective for treating sleep-onset insomnia, i.e., a subject's difficulty in falling asleep, there are no drugs currently indicated for treating sleep maintenance insomnia, i.e., maintaining a subject's sleep throughout a normal sleep period after falling asleep. Therefore, there is also a need for improved pharmaceutical treatments for maintaining sleep in subjects in need of such treatment.

SUMMARY OF THE INVENTION

The present invention relates to benzisoxazole compounds which modulate sleep. In one aspect, the invention relates to a compound of Formula I:

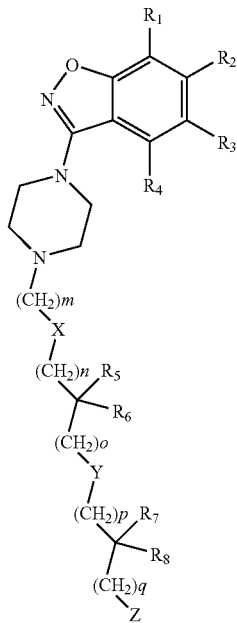

or a pharmaceutically effective salt, solvate, hydrate, or prodrug thereof, wherein m n, o, p, q are, individually, 0, 1, 2, 3, 4, 5, or 6; X and Y are, individually, absent, O, S, C(O), SO or $SO_2$; $R_1$, $R_2$, $R_3$, and $R_4$ are, independently selected from H, F, Cl, Br, I, $CF_3$, $C_1$, $C_2$, $C_3$, $C_4$, $C_5$ or $C_6$ straight chain alkyl, $C_3$, $C_4$, $C_5$ or $C_6$ branched alkyl, $C_3$, $C_4$, $C_5$, $C_6$, $C_7$ or $C_8$ cycloalkyl, $C_3$, $C_4$, $C_5$, $C_6$, or $C_7$ heterocyclyl, $OCF_3$, $CH_2OCH_3$, $CH_2CH_2OCH_3$, $CH_2OCH_2CH_3$, $C_1$, $C_2$, $C_3$, $C_4$, $C_5$ or $C_6$ alkoxy, and $C_1$, $C_2$, $C_3$, $C_4$, $C_5$ or $C_6$ hydroxyalkyl; $R_5$, $R_6$, $R_7$, and $R_8$ are, independently, H, $C_1$, $C_2$, $C_3$, $C_4$, $C_5$, or $C_6$ straight chain alkyl, $C_3$, $C_4$, $C_5$ or $C_6$ branched alkyl; $R_5$ and $R_6$ together with the carbon to which they are attached, are connected to form a spiro ring of size 3, 4, 5, 6, or 7;

$R_7$ and $R_8$ together with the carbon to which they are attached, are connected to form a spiro ring of size 3, 4, 5, 6, or 7; or substituents on two different atoms are connected to form a ring of size 3, 4, 5, 6, or 7; and Z is selected from $CO_2H$, $CO_2R_9$, where $R_9$ is $C_1$, $C_2$, $C_3$, $C_4$, $C_5$ or $C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2N$-alkyl, $CONHS(O)_2N$-cycloalkyl, $CONHS(O)_2N$-heteroalkyl, $CONHS(O)_2N$-aryl, $CONHS(O)_2N$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

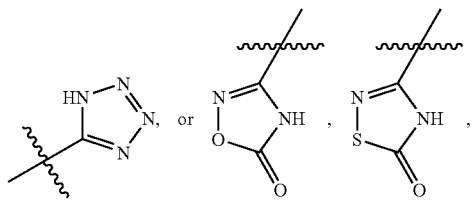

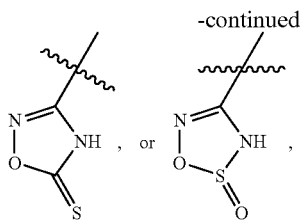, or provided that when m is zero, X is absent.

In one embodiment, $R_1$, $R_2$, $R_3$, and $R_4$ are each H. In another embodiment, $R_1$, $R_3$, and $R_4$ are each H. In another embodiment, $R_1$, $R_2$, and $R_4$ are each H. In another embodiment, at least one of $R_2$ and $R_3$ is not H. In another embodiment, $R_1$ is H. In another embodiment, $R_2$ and $R_3$ are not H. In one embodiment, at least one of $R_2$ and $R_3$ is selected from $C_1$-$C_6$ alkyl or $C_1$-$C_6$ alkoxy. In another embodiment, at least one of $R_2$ and $R_3$ is selected from $CH_3$ or $OCH_3$. In one embodiment, $R_2$ is $C_1$-$C_6$ alkyl. In another embodiment, $R_2$ is $CH_3$. In another embodiment, $R_3$ is $CH_3$. In one embodiment, $R_3$ is $C_1$-$C_6$ alkoxy. In another embodiment, $R_3$ is $OCH_3$.

In one embodiment, X and Y are absent. In another embodiment, $R_5$ and $R_6$ together with the carbon to which they are attached are absent. In one embodiment, $R_5$ and $R_6$ are each H. In one embodiment, $R_5$ and $R_6$ are each $C_1$-$C_6$ alkyl. In another embodiment, $R_5$ and $R_6$ are each methyl. In another embodiment, $R_5$ and $R_6$ are each ethyl. In another embodiment, $R_5$ and $R_6$ together with the carbon to which they are attached are connected to form a spiro cyclopropyl ring.

In one embodiment, the sum of m, n, o, p, and q is 1, 2, 3, 4, 5, or 6. In another embodiment, the sum of m, n, o, p, and q is 1, 2, 3, or 4. In another embodiment, the sum of m, n, o, p, and q is 1, 2, or 3. In another embodiment, the sum of m, n, o, p, and q is 1. In another embodiment, the sum of m, n, o, p, and q is 2. In another embodiment, the sum of m, n, o, p, and q is 3. In one embodiment, q is 0.

In one embodiment, any hydrogen in the $CH_2$ groups in the linker is substituted with a substituent selected from H, F, Cl, Br, I, $CF_3$, $CH_3$, $C_2$ $C_3$, $C_4$, $C_5$, or $C_6$ straight chain alkyl, $C_3$, $C_4$, $C_5$, or $C_6$ branched alkyl, $C_3$, $C_4$, $C_5$, $C_6$, $C_7$ or $C_8$ cycloalkyl, $C_3$, $C_4$, $C_5$, $C_6$, $C_7$ or $C_8$ heterocyclyl, $C_1$, $C_2$, $C_3$, $C_4$, $C_5$, $C_6$ alkoxy, $OCF_3$, $CH_2OCH_3$, $CH_2CH_2OCH_3$, $CH_2OCH_2CH_3$, or $C_1$, $C_2$, $C_3$, $C_4$, $C_5$ or $C_6$ hydroxyalkyl.

In one embodiment, $R_7$ and $R_8$ are each H. In one embodiment, $R_7$ and $R_8$ are each $C_1$-$C_6$ alkyl. In another embodiment, $R_7$ and $R_8$ are each methyl. In another embodiment, $R_7$ and $R_8$ are each ethyl. In another embodiment, $R_7$ and $R_8$ together with the carbon to which they are attached are connected to form a spiro cyclopropyl ring.

In one embodiment, Z is COOH. In another embodiment, Z is selected from $CONHS(O)_2$-alkyl, $CONHS(O)_2$-cycloalkyl, $CONHS(O)_2$-heteroalkyl, $CONHS(O)_2$-aryl, and $CONHS(O)_2$-heteroaryl. In another embodiment, Z is selected from $CONHSO_2$-alkyl and $CONHSO_2$-heteroalkyl. In one embodiment, Z is $CONHSO_2CH_3$. In another embodiment, Z is $CONHSO_2CH(CH_3)_2$. In another embodiment, Z is

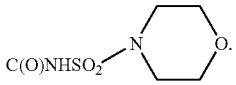

In one embodiment, the salt is an acid addition salt. In another embodiment, the salt is a hydrochloride salt.

In another aspect, the invention relates to a compound of Formula II:

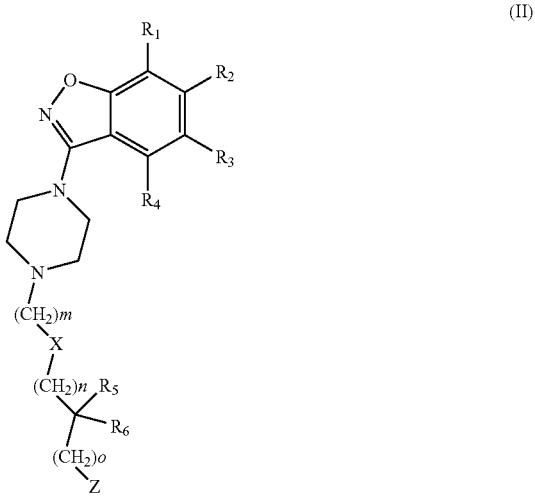

(II)

or a pharmaceutically effective salt, solvate, hydrate, or prodrug thereof, wherein m, n, and o are, individually, 0, 1, 2, 3, 4, 5, or 6; X is absent, O, S, C(O), SO or $SO_2$; $R_1$, $R_2$, $R_3$, and $R_4$ are, independently selected from H, F, Cl, Br, $CF_3$, $CH_3$, $CH_2CH_3$, $CH(CH_3)_2$, cyclopropyl, $OCH_3$, $OCF_3$, $CH_2OCH_3$ and $CH_2OCH_2CH_3$; $R_5$, and $R_6$, are, independently, H, $C_1$-$C_5$ straight chain alkyl; $C_3$-$C_6$ branched alkyl, or $R_5$ and $R_6$ together with the carbon to which they are attached, are connected to form a spiro ring of size 3, 4, 5, 6, or 7; and Z is COOH, COOR$_9$, where $R_9$ is $C_1$-$C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2N$-alkyl; $CONHS(O)_2N$-heteroalkyl; $CONHS(O)_2N$-aryl; $CONHS(O)_2N$-heteroaryl; or tetrazole, provided that when m is zero, X is absent.

In one embodiment, $R_1$, $R_2$, $R_3$, and $R_4$ are each H. In another embodiment, $R_1$, $R_3$, and $R_4$ are each H. In another embodiment, $R_1$, $R_2$, and $R_4$ are each H. In another embodiment, at least one of $R_2$ and $R_3$ is not H. In another embodiment, $R_2$ and $R_3$ are not H. In another embodiment, $R_1$ is H. In one embodiment, at least one of $R_2$ and $R_3$ is selected from $CH_3$ or $OCH_3$. In another embodiment, $R_2$ is $CH_3$. In another embodiment, $R_3$ is $CH_3$. In another embodiment, $R_3$ is $OCH_3$.

In one embodiment, X is absent. In one embodiment, the sum of m, n, and o is 1. In another embodiment, the sum of m, n, and o is 2. In one embodiment, o is zero.

In one embodiment, $R_5$ and $R_6$ are each H. In one embodiment, $R_5$ and $R_6$ are each $C_1$-$C_5$ alkyl. In another embodiment, $R_5$ and $R_6$ are each methyl. In another embodiment, $R_5$ and $R_6$ are each ethyl. In another embodiment, $R_5$ and $R_6$ together with the carbon to which they are attached are connected to form a spiro cyclopropyl ring.

In one embodiment, Z is COOH. In another embodiment, Z is selected from CONHS(O)$_2$-alkyl, CONHS(O)$_2$-cycloalkyl, CONHS(O)$_2$-heteroalkyl, CONHS(O)$_2$-aryl, and CONHS(O)$_2$-heteroaryl. In another embodiment, Z is selected from CONHSO$_2$-alkyl and CONHSO$_2$-heteroalkyl. In one embodiment, Z is CONHSO$_2$CH$_3$. In another embodiment, Z is CONHSO$_2$CH(CH$_3$)$_2$. In another embodiment, Z is

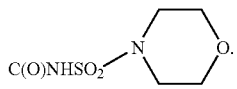

In one embodiment, the salt is an acid addition salt. In another embodiment, the salt is a hydrochloride salt.

In another aspect, the invention relates to a compound of Formula III:

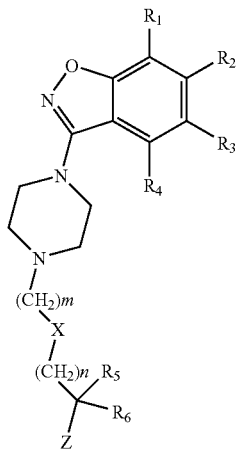

(III)

or a pharmaceutically effective salt, solvate, hydrate, or prodrug, thereof, wherein m and n are, individually, 0, 1, 2, 3, or 4; X is absent, O, S, C(O), SO or SO$_2$; R$_1$, R$_2$, R$_3$, and R$_4$ are, independently, selected from H, F, Cl, Br, CF$_3$, CH$_3$, CH$_2$CH$_3$, CH(CH$_3$)$_2$, cyclopropyl, OCH$_3$, OCF$_3$, CH$_2$OCH$_3$, and CH$_2$OCH$_2$CH$_3$; R$_5$, and R$_6$, are, independently, H, C$_1$, C$_2$, C$_3$, C$_4$, C$_5$ straight chain alkyl; C$_3$, C$_4$, C$_5$, C$_6$ branched alkyl, or R$_5$, and R$_6$, together with the carbon to which they are attached, are connected to form a spiro ring of size 3, 4, 5, 6, or 7; and Z is selected from CO$_2$H, CONHS(O)$_2$-alkyl, CONHS(O)$_2$-cycloalkyl, CONHS(O)$_2$-heteroalkyl, CONHS(O)$_2$-aryl, CONHS(O)$_2$-heteroaryl, and tetrazole; provided that when m is zero, X is absent.

In one embodiment, R$_1$, R$_2$, R$_3$, and R$_4$ are each H. In another embodiment, R$_1$, R$_3$, and R$_4$ are each H. In another embodiment, R$_1$, R$_2$, and R$_4$ are each H. In one embodiment, at least one of R$_2$ and R$_3$ is not H. In another embodiment, R$_2$ and R$_3$ are not H. In another embodiment, R$_1$ is H. In another embodiment, at least one of R$_2$ and R$_3$ is selected from CH$_3$ or OCH$_3$. In another embodiment, R$_2$ is CH$_3$. In another embodiment, R$_3$ is CH$_3$. In another embodiment, R$_3$ is OCH$_3$.

In one embodiment, X is absent. In one embodiment, the sum of m and n is 1. In another embodiment, the sum of m and n is 2.

In one embodiment, R$_5$ and R$_6$ are each H. In one embodiment, R$_5$ and R$_6$ are each C$_1$-C$_6$ alkyl. In another embodiment, R$_5$ and R$_6$ are each methyl. In another embodiment, R$_5$ and R$_6$ are each ethyl. In another embodiment, R$_5$ and R$_6$ together with the carbon to which they are attached are connected to form a spiro cyclopropyl ring.

In one embodiment, Z is COOH. In another embodiment, Z is selected from CONHS(O)$_2$-alkyl, CONHS(O)$_2$-cycloalkyl, CONHS(O)$_2$-heteroalkyl, CONHS(O)$_2$-aryl, and CONHS(O)$_2$-heteroaryl. In another embodiment, Z is selected from CONHSO$_2$-alkyl and CONHSO$_2$-heteroalkyl. In one embodiment, Z is CONHSO$_2$CH$_3$. In one embodiment, Z is CONHSO$_2$CH(CH$_3$)$_2$. In another embodiment, Z is

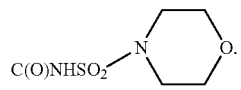

In one embodiment, the salt is an acid addition salt. In another embodiment, the salt is a hydrochloride salt.

In another aspect, the invention relates to a compound of Formula IV:

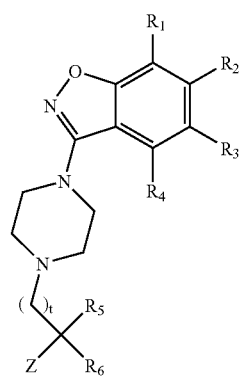

(IV)

or a pharmaceutically effective salt, solvate, hydrate, or prodrug thereof wherein t is 1, 2, 3, 4, 5, or 6; R$_1$, R$_2$, R$_3$, and R$_4$ are, independently, H, F, Cl, Br, CF$_3$, CH$_3$, OH, OCH$_3$, CH$_2$OCH$_3$, or CH$_2$OCH$_2$CH$_3$; R$_5$-R$_6$ are H, CH$_3$, CH$_2$CH$_3$, or R$_5$ and R$_6$, together with the carbon to which they are attached, are connected to form a spiro ring of size 3, 4, 5, 6, or 7; and Z is selected from CO$_2$H, CONHS(O)$_2$-alkyl, CONHS(O)$_2$-cycloalkyl, CONHS(O)$_2$-heteroalkyl, and tetrazole.

In one embodiment, R$_1$, R$_2$, R$_3$, and R$_4$ are each H. In another embodiment, R$_1$, R$_3$, and R$_4$ are each H. In another embodiment, R$_1$, R$_2$, and R$_4$ are each H. In another embodiment, at least one of R$_2$ and R$_3$ is not H. In another embodiment, R$_2$ and R$_3$ are not H. In another embodiment, R$_1$ is H. In another embodiment, at least one of R$_2$ and R$_3$ is selected from CH$_3$ or OCH$_3$. In another embodiment, R$_2$ is CH$_3$. In another embodiment, R$_3$ is CH$_3$. In another embodiment, R$_3$ is OCH$_3$.

In one embodiment, t is 1. In another embodiment, t is 2.

In one embodiment, R$_5$ and R$_6$ are each H. In another embodiment, R$_5$ and R$_6$ are each methyl. In another embodiment, R$_5$ and R$_6$ are each ethyl. In another embodiment, R$_5$ and R$_6$ together with the carbon to which they are attached are connected to form a spiro cyclopropyl ring.

In one embodiment, Z is COOH. In another embodiment, Z is selected from CONHSO$_2$-alkyl and CONHSO$_2$-heteroalkyl. In another embodiment, Z is CONHSO$_2$CH$_3$. In another embodiment, Z is CONHSO$_2$CH(CH$_3$)$_2$. In another embodiment, Z is
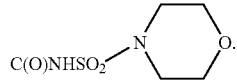
In one embodiment, the salt is an acid addition salt. In another embodiment, the salt is a hydrochloride salt.
In another aspect, the invention relates to a compound selected from:
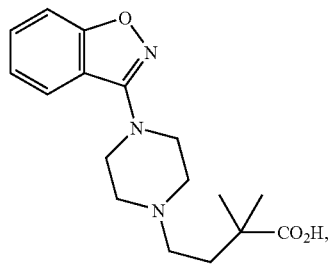
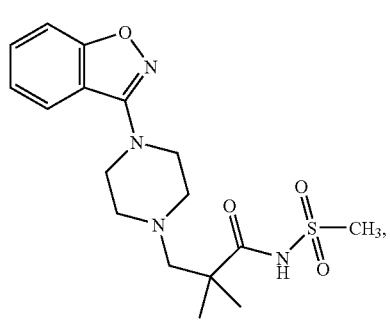
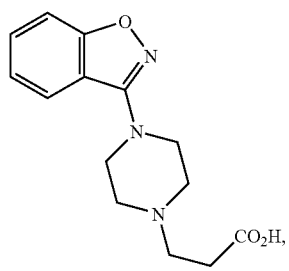
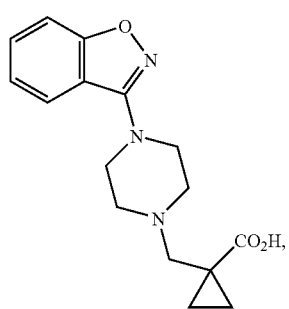
-continued
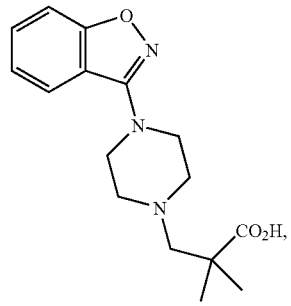
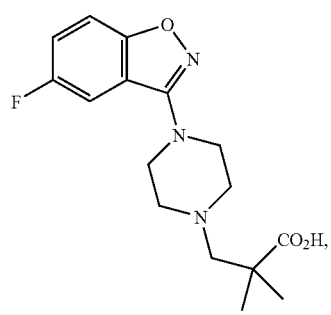
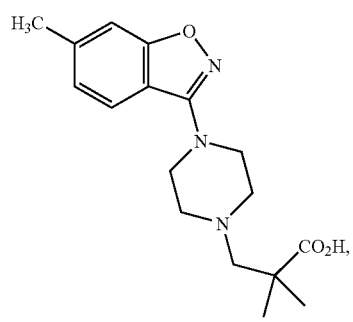
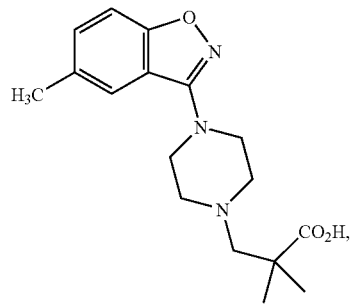
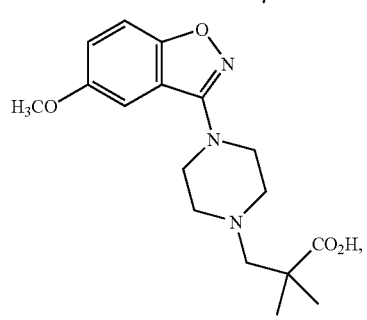

-continued

In another aspect, the invention relates to a pharmaceutical composition comprising a compound of Formula I:

(I)

wherein m n, o, p, q are, individually, 0, 1, 2, 3, 4, 5, or 6; X and Y are, individually, absent, O, S, C(O), SO or $SO_2$; $R_1$, $R_2$, $R_3$, and $R_4$ are, independently selected from H, F, Cl, Br, I, $CF_3$, $C_1$, $C_2$, $C_3$, $C_4$, $C_5$ or $C_6$ straight chain alkyl, $C_3$, $C_4$, $C_5$ or $C_6$ branched alkyl, $C_3$, $C_4$, $C_5$, $C_6$, $C_7$ or $C_8$ cycloalkyl, $C_3$, $C_4$, $C_5$, $C_6$, or $C_7$ heterocyclyl, $OCF_3$, $CH_2OCH_3$, $CH_2CH_2OCH_3$, $CH_2OCH_2CH_3$, $C_1$, $C_2$, $C_3$, $C_4$, $C_5$ or $C_6$ alkoxy, and $C_1$, $C_2$, $C_3$, $C_4$, $C_5$ or $C_6$ hydroxyalkyl; $R_5$, $R_6$, $R_7$, and $R_8$ are, independently, H, $C_1$, $C_2$, $C_3$, $C_4$, $C_5$, or $C_6$ straight chain alkyl, $C_3$, $C_4$, $C_5$ or $C_6$ branched alkyl; $R_5$ and $R_6$ together with the carbon to which they are attached, are connected to form a spiro ring of size 3, 4, 5, 6, or 7; $R_7$ and $R_8$ together with the carbon to which they are attached, are connected to form a spiro ring of size 3, 4, 5, 6, or 7; or substituents on two different atoms are connected to form a ring of size 3, 4, 5, 6, or 7; and Z is selected from $CO_2H$, $CO_2R_9$, where $R_9$ is $C_1$, $C_2$, $C_3$, $C_4$, $C_5$ or $C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2 NHCO$-cycloalkyl, $S(O)_2NHCO$-heteroalkyl, $S(O)_2 NHCO$-aryl, $S(O)_2NHCO$-heteroaryl, $CONHS(O)_2N$-alkyl, $CONHS(O)_2N$-cycloalkyl, $CONHS(O)_2N$-heteroalkyl, $CONHS(O)_2N$-aryl, $CONHS(O)_2N$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

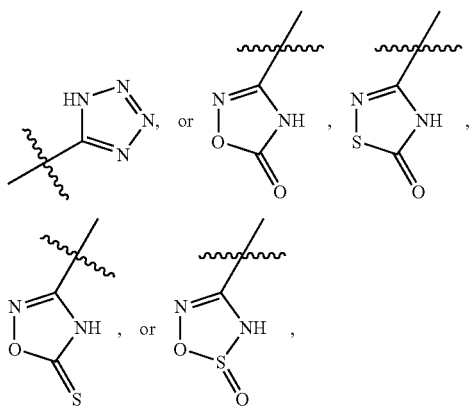

provided that when m is zero, X is absent, or a salt, solvate, hydrate, or prodrug thereof, and at least one pharmaceutically acceptable excipient.

In another aspect, the invention relates to a pharmaceutical composition comprising a compound of Formula II:

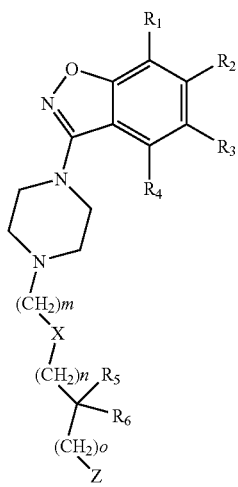

(II)

wherein m, n, and o are, individually, 0, 1, 2, 3, 4, 5, or 6; X is absent, O, S, C(O), SO or $SO_2$; $R_1$, $R_2$, $R_3$, and $R_4$ are, independently selected from H, F, Cl, Br, $CF_3$, $CH_3$, $CH_2CH_3$, $CH(CH_3)_2$, cyclopropyl, $OCH_3$, $OCF_3$, $CH_2OCH_3$ and $CH_2OCH_2CH_3$; $R_5$, and $R_6$, are, independently, H, $C_1$, $C_2$, $C_3$, $C_4$, $C_5$ straight chain alkyl; $C_3$, $C_4$, $C_5$, $C_6$ branched alkyl, or $R_5$ and $R_6$ together with the carbon to which they are attached, are connected to form a spiro ring of size 3, 4, 5, 6, or 7; and Z is COOH, $COOR_9$, where $R_9$ is $C_1$-$C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2 NHCO$-heteroaryl, $CONHS(O)_2N$-alkyl; $CONHS(O)_2N$-heteroalkyl; $CONHS(O)_2N$-aryl; $CONHS(O)_2N$-heteroaryl; or tetrazole, provided that when m is zero, X is absent, or a salt, solvate, hydrate, or prodrug thereof, and at least one pharmaceutically acceptable excipient.

In another aspect, the invention relates to a pharmaceutical composition comprising a compound of Formula III:

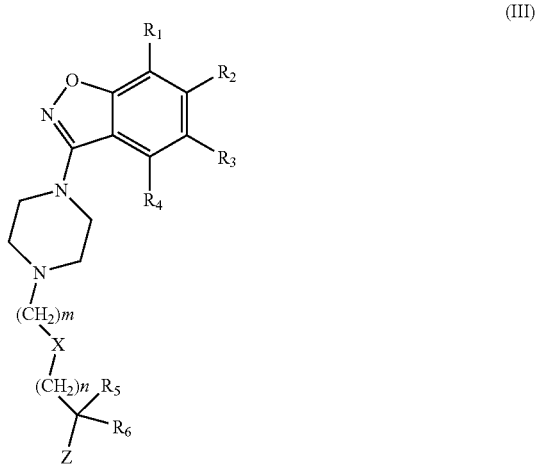

(III)

wherein m and n are, individually, 0, 1, 2, 3, or 4, X is absent, O, S, C(O), SO or $SO_2$; $R_1$, $R_2$, $R_3$, and $R_4$ are, independently, selected from H, F, Cl, Br, $CF_3$, $CH_3$, $CH_2CH_3$, $CH(CH_3)_2$, cyclopropyl, $OCH_3$, $OCF_3$, $CH_2OCH_3$, and $CH_2OCH_2CH_3$; $R_5$, and $R_6$, are, independently, H, $C_1$-$C_5$ straight chain alkyl; $C_3$-$C_6$ branched alkyl, or $R_5$, and $R_6$, together with the carbon to which they are attached, are connected to form a spiro ring of size 3, 4, 5, 6, or 7; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, and tetrazole; provided that when m is zero, X is absent, or a salt, solvate, hydrate, or prodrug thereof, and at least one pharmaceutically acceptable excipient.

In another aspect, the invention relates to a pharmaceutical composition comprising a compound of Formula IV:

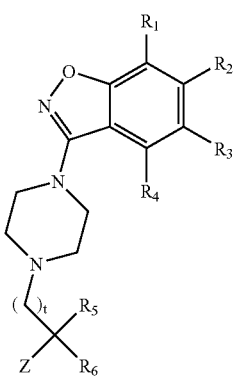

(IV)

wherein t is 1, 2, 3, 4, 5, or 6; $R_1$, $R_2$, $R_3$, and $R_4$ are, independently, H, F, Cl, Br, $CF_3$, $CH_3$, OH, $OCH_3$, $CH_2OCH_3$, or $CH_2OCH_2CH_3$; $R_5$-$R_6$ are H, $CH_3$, $CH_2CH_3$, or $R_5$ and $R_6$, together with the carbon to which they are attached, are connected to form a spiro ring of size 3, 4, 5, 6, or 7; and Z is selected from $CO_2H$, $CONHS(O)_2$-alkyl, $CONHS(O)_2$-cycloalkyl, $CONHS(O)_2$-heteroalkyl, and tetrazole.

In another aspect, the invention relates to a method of treating a subject for a sleep disorder, comprising administering to a subject in need of treatment for a sleeping disorder a therapeutically effective amount of a compound represented by Formula I:

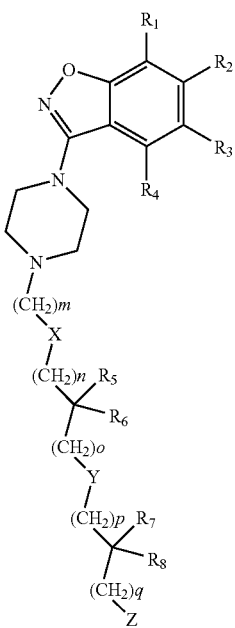

(I)

or a pharmaceutically effective salt, solvate, hydrate, or prodrug thereof, wherein m n, o, p, q are, individually, 0, 1, 2, 3, 4, 5, or 6; X and Y are, individually, absent, O, S, C(O), SO or $SO_2$;

$R_1$, $R_2$, $R_3$, and $R_4$ are, independently selected from H, F, Cl, Br, I, $CF_3$, $C_1$, $C_2$, $C_3$, $C_4$, $C_5$ or $C_6$ straight chain alkyl, $C_3$, $C_4$, $C_5$ or $C_6$ branched alkyl, $C_3$, $C_4$, $C_5$, $C_6$, $C_7$ or $C_8$ cycloalkyl, $C_3$, $C_4$, $C_5$, $C_6$, or $C_7$ heterocyclyl, $OCF_3$, $CH_2OCH_3$, $CH_2CH_2OCH_3$, $CH_2OCH_2CH_3$, $C_1$, $C_2$, $C_3$, $C_4$, $C_5$ or $C_6$ alkoxy, and $C_1$, $C_2$, $C_3$, $C_4$, $C_5$ or $C_6$ hydroxyalkyl; $R_5$, $R_6$, $R_7$, and $R_8$ are, independently, H, $C_1$, $C_2$, $C_3$, $C_4$, $C_5$, or $C_6$ straight chain alkyl, $C_3$, $C_4$, $C_5$ or $C_6$ branched alkyl; $R_5$ and $R_6$ together with the carbon to which they are attached, are connected to form a spiro ring of size 3, 4, 5, 6, or 7; $R_7$ and $R_8$ together with the carbon to which they are attached, are connected to form a spiro ring of size 3, 4, 5, 6, or 7; or substituents on two different atoms are connected to form a ring of size 3, 4, 5, 6, or 7; and Z is selected from $CO_2H$, $CO_2R_9$, where $R_9$ is $C_1$, $C_2$, $C_3$, $C_4$, $C_5$ or $C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2N$-alkyl, $CONHS(O)_2N$-cycloalkyl, $CONHS(O)_2N$-heteroalkyl, $CONHS(O)_2N$-aryl, $CONHS(O)_2N$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

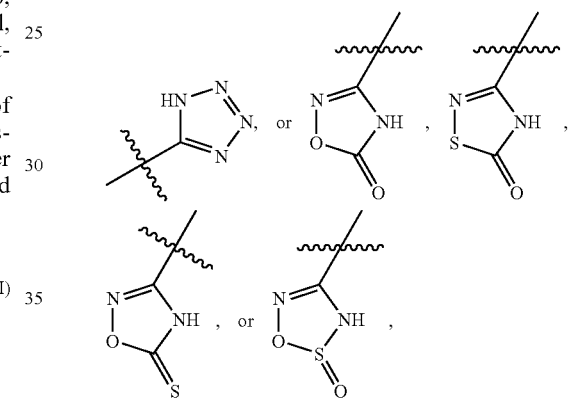

provided that when m is zero, X is absent.

In one embodiment, the subject is a human. In one embodiment, the sleep disorder is selected from the group consisting of insomnia, hypersomnia, narcolepsy, sleep apnea syndrome, parasomnia, restless leg syndrome, and circadian rhythm abnormality. In another embodiment, the sleep disorder is circadian rhythm abnormality. In another embodiment, the circadian rhythm abnormality is selected from the group consisting of jet lag, shift-work disorders, and delayed or advanced sleep phase syndrome. In one embodiment, the sleep disorder is insomnia. In another embodiment, insomnia is treated in the subject by effecting at least one action selected from the group consisting of decreasing the time to sleep onset, increasing the average sleep bout length, and increasing the maximum sleep bout length. In one embodiment, the compound or pharmaceutically acceptable salt, solvate, hydrate, or prodrug, is administered as a pharmaceutical composition comprising at least one pharmaceutical acceptable excipient. In another embodiment, the compound or pharmaceutically acceptable salt, solvate, hydrate, or prodrug is co-administered with one or more additional therapies.

In another aspect, the invention relates to a method of treating a subject for a sleep disorder, comprising administering to a subject in need of treatment for a sleeping disorder a therapeutically effective amount of a compound represented by Formula II:

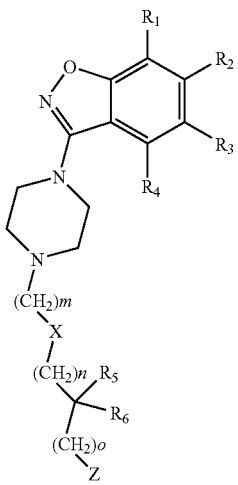

(II)

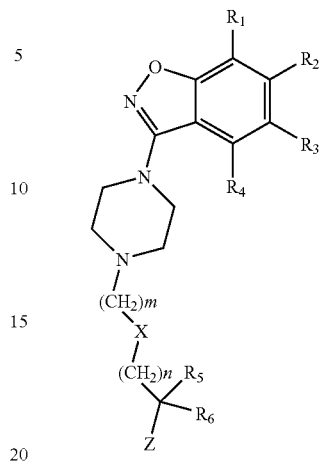

(III)

or a pharmaceutically effective salt, solvate, hydrate, or prodrug thereof, wherein m, n, and o are, individually, 0, 1, 2, 3, 4, 5, or 6; X is absent, O, S, C(O), SO or $SO_2$; $R_1$, $R_2$, $R_3$, and $R_4$ are, independently selected from H, F, Cl, Br, $CF_3$, $CH_3$, $CH_2CH_3$, $CH(CH_3)_2$, cyclopropyl, $OCH_3$, $OCF_3$, $CH_2OCH_3$ and $CH_2OCH_2CH_3$; $R_5$, and $R_6$, are, independently, H, $C_1$-$C_5$ straight chain alkyl; $C_3$-$C_6$ branched alkyl, or $R_5$ and $R_6$ together with the carbon to which they are attached, are connected to form a spiro ring of size 3, 4, 5, 6, or 7; and Z is COOH, $COOR_9$, where $R_9$ is $C_1$-$C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2N$-alkyl; $CONHS(O)_2N$-heteroalkyl; $CONHS(O)_2N$-aryl; $CONHS(O)_2N$-heteroaryl; or tetrazole, provided that when m is zero, X is absent.

In one embodiment, the subject is a human. In another embodiment, the sleep disorder is selected from the group consisting of insomnia, hypersomnia, narcolepsy, sleep apnea syndrome, parasomnia, restless leg syndrome, and circadian rhythm abnormality. In another embodiment, the sleep disorder is circadian rhythm abnormality. In another embodiment, the circadian rhythm abnormality is selected from the group consisting of jet lag, shift-work disorders, and delayed or advanced sleep phase syndrome. In one embodiment, the sleep disorder is insomnia. In another embodiment, insomnia is treated in the subject by effecting at least one action selected from the group consisting of decreasing the time to sleep onset, increasing the average sleep bout length, and increasing the maximum sleep bout length. In another embodiment, the compound or pharmaceutically acceptable salt, solvate, hydrate, or prodrug, is administered as a pharmaceutical composition comprising at least one pharmaceutical acceptable excipient. In another embodiment, the compound or pharmaceutically acceptable salt, solvate, hydrate, or prodrug is co-administered with one or more additional therapies.

In another aspect, the invention relates to a method of treating a subject for a sleep disorder, comprising administering to a subject in need of treatment for a sleeping disorder a therapeutically effective amount of a compound represented by Formula III:

or a pharmaceutically effective salt, solvate, hydrate, or prodrug thereof, wherein m and n are, individually, 0, 1, 2, 3, or 4; X is absent, O, S, C(O), SO or $SO_2$; $R_1$, $R_2$, $R_3$, and $R_4$ are, independently, selected from H, F, Cl, Br, $CF_3$, $CH_3$, $CH_2CH_3$, $CH(CH_3)_2$, cyclopropyl, $OCH_3$, $OCF_3$, $CH_2OCH_3$, and $CH_2OCH_2CH_3$; $R_5$, and $R_6$, are, independently, H, $C_1$-$C_5$ straight chain alkyl; $C_3$-$C_6$ branched alkyl, or $R_5$, and $R_6$, together with the carbon to which they are attached, are connected to form a spiro ring of size 3, 4, 5, 6, or 7; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, and tetrazole; provided that when m is zero, X is absent.

In one embodiment, the subject is a human. In another embodiment, the sleep disorder is selected from the group consisting of insomnia, hypersomnia, narcolepsy, sleep apnea syndrome, parasomnia, restless leg syndrome, and circadian rhythm abnormality. In another embodiment, the sleep disorder is circadian rhythm abnormality. In another embodiment, the circadian rhythm abnormality is selected from the group consisting of jet lag, shift-work disorders, and delayed or advanced sleep phase syndrome. In one embodiment, the sleep disorder is insomnia. In one embodiment, insomnia is treated in the subject by effecting at least one action selected from the group consisting of decreasing the time to sleep onset, increasing the average sleep bout length, and increasing the maximum sleep bout length. In another embodiment, the compound or pharmaceutically acceptable salt, solvate, hydrate, or prodrug, is administered as a pharmaceutical composition comprising at least one pharmaceutical acceptable excipient. In another embodiment, the compound or pharmaceutically acceptable salt, solvate, hydrate, or prodrug is co-administered with one or more additional therapies.

In another aspect, the invention relates to a method of treating a subject for a sleep disorder, comprising administering to a subject in need of treatment for a sleeping disorder a therapeutically effective amount of a compound represented by Formula IV:

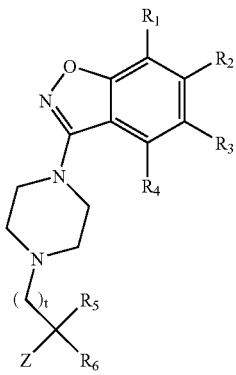

(IV)

or a pharmaceutically effective salt, solvate, hydrate, or prodrug thereof wherein t is 1, 2, 3, 4, 5, or 6; $R_1$, $R_2$, $R_3$, and $R_4$ are, independently, H, F, Cl, Br, $CF_3$, $CH_3$, OH, $OCH_3$, $CH_2OCH_3$, or $CH_2OCH_2CH_3$; $R_5$-$R_6$ are H, $CH_3$, $CH_2CH_3$, or $R_5$ and $R_6$, together with the carbon to which they are attached, are connected to form a spiro ring of size 3, 4, 5, 6, or 7; and Z is selected from $CO_2H$, $CONHS(O)_2$-alkyl, $CONHS(O)_2$-cycloalkyl, $CONHS(O)_2$-heteroalkyl, and tetrazole.

In one embodiment, the subject is a human. In another embodiment, the sleep disorder is selected from the group consisting of insomnia, hypersomnia, narcolepsy, sleep apnea syndrome, parasomnia, restless leg syndrome, and circadian rhythm abnormality. In another embodiment, the sleep disorder is circadian rhythm abnormality. In another embodiment, the circadian rhythm abnormality is selected from the group consisting of jet lag, shift-work disorders, and delayed or advanced sleep phase syndrome. In another embodiment, the sleep disorder is insomnia. In another embodiment, insomnia is treated in the subject by effecting at least one action selected from the group consisting of decreasing the time to sleep onset, increasing the average sleep bout length, and increasing the maximum sleep bout length. In one embodiment, the compound or pharmaceutically acceptable salt, solvate, hydrate, or prodrug, is administered as a pharmaceutical composition comprising at least one pharmaceutical acceptable excipient. In another embodiment, the compound or pharmaceutically acceptable salt, solvate, hydrate, or prodrug is co-administered with one or more additional therapies. In another embodiment, the compound is selected from the group of compounds consisting of:

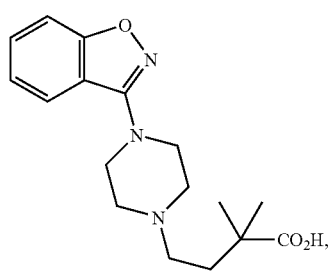

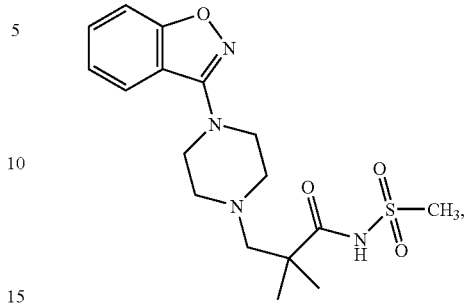

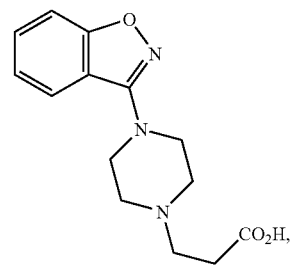

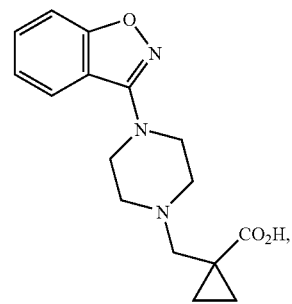

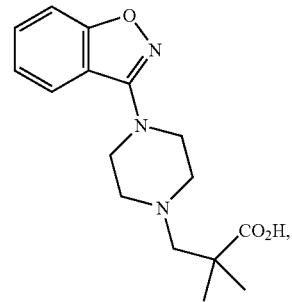

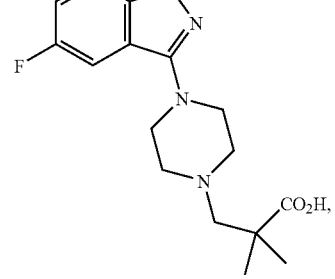

-continued
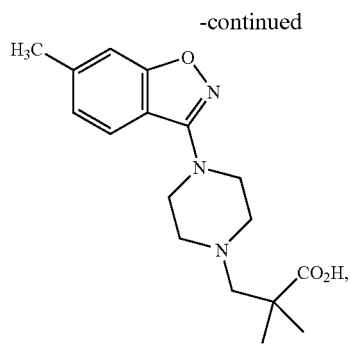
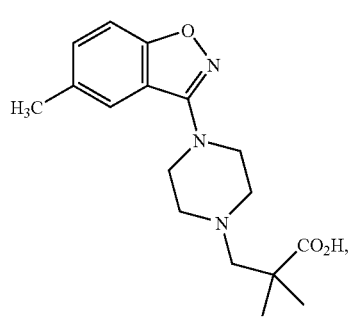
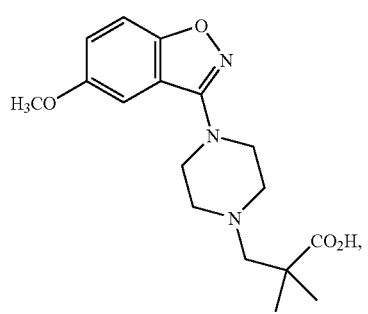
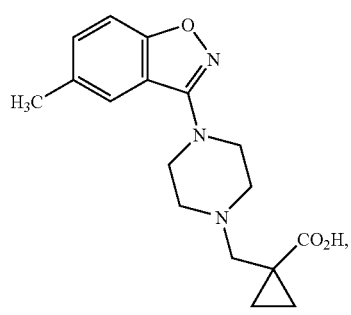
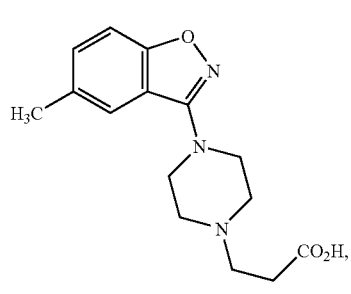
-continued
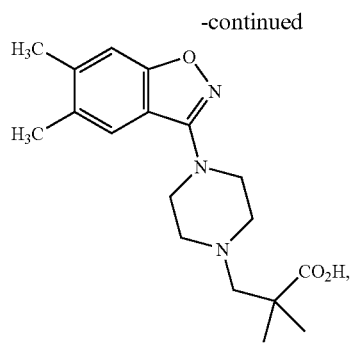
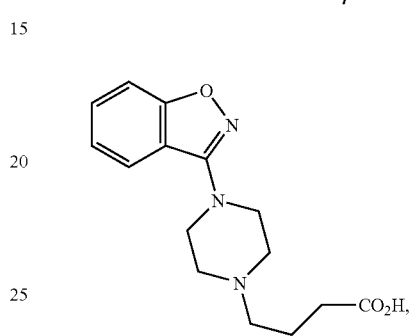
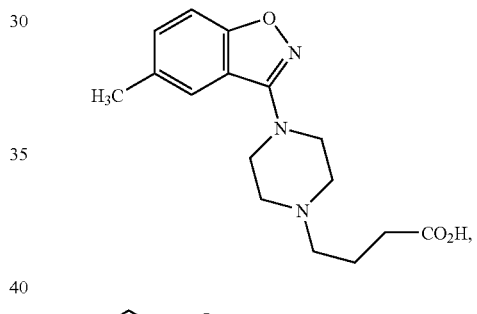
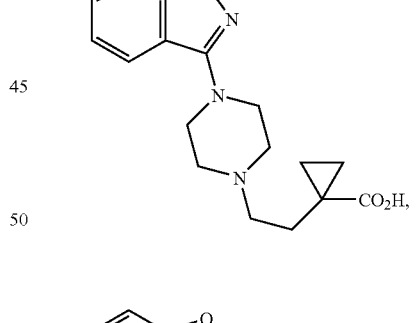
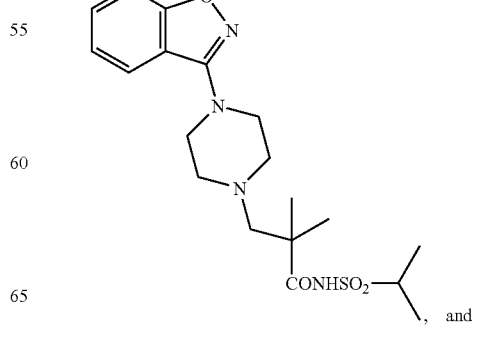
, and -continued

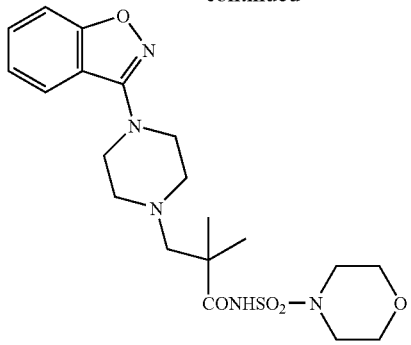

DETAILED DESCRIPTION

The details of at least one embodiments of the invention are set forth in the accompanying description below. Although any methods and materials similar or equivalent to those described herein can be used in the practice or testing of the present invention, the methods and materials of the present invention are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

The invention relates to novel benzisoxazole piperazine compositions. In one aspect, the invention provides a compound according to Formula I:

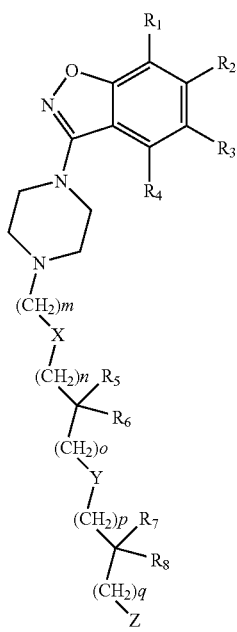

(I)

or a pharmaceutically effective salt thereof, wherein m n, o, p, q are, individually, 0, 1, 2, 3, 4, 5, or 6; X and Y are, individually, absent, O, S, C(O), SO or $SO_2$; $R_1$, $R_2$, $R_3$, and $R_4$ are, independently selected from H, F, Cl, Br, I, $CF_3$, $CH_3$, $C_2$, $C_3$, $C_4$, $C_5$ or $C_6$ straight chain alkyl, $C_3$, $C_4$, $C_5$ or $C_6$ branched alkyl, $C_3$, $C_4$, $C_5$, $C_6$, $C_7$ or $C_8$ cycloalkyl, $C_3$, $C_4$, $C_5$, $C_6$, or $C_7$ heterocyclyl, $OCH_3$, $OCF_3$, $CH_2OCH_3$, $CH_2CH_2OCH_3$, $CH_2OCH_2CH_3$, $C_1$, $C_2$, $C_3$, $C_4$, $C_5$ or $C_6$ alkoxy, and $C_1$, $C_2$, $C_3$, $C_4$, $C_5$ or $C_6$ hydroxyalkyl; any hydrogen in the $CH_2$ groups in the linker is optionally substituted with H, F, Cl, Br, I, $CF_3$, $CH_3$, $C_2$ $C_3$, $C_4$, $C_5$, or $C_6$ straight chain alkyl, $C_3$, $C_4$, $C_5$, or $C_6$ branched alkyl, $C_3$, $C_4$, $C_5$, $C_6$, $C_7$ or $C_8$ cycloalkyl, $C_3$, $C_4$, $C_5$, $C_6$, $C_7$ or $C_8$ heterocyclyl, $C_1$, $C_2$, $C_3$, $C_4$, $C_5$, $C_6$ alkoxy, $OCF_3$, $CH_2OCH_3$, $CH_2CH_2OCH_3$, $CH_2OCH_2CH_3$, or $C_1$, $C_2$, $C_3$, $C_4$, $C_5$ or $C_6$ hydroxyalkyl, provided that such substitution does not result in the formation of an unstable functionality; $R_5$, $R_6$, $R_7$, and $R_8$ are, independently, H, $C_1$, $C_2$, $C_3$, $C_4$, $C_5$, or $C_6$ straight chain alkyl, $C_3$, $C_4$, $C_5$ or $C_6$ branched alkyl; $R_5$ and $R_6$ together with the carbon to which they are attached, are connected to form a spiro ring of size 3, 4, 5, 6, or 7; $R_7$ and $R_8$ together with the carbon to which they are attached, are connected to form a Spiro ring of size 3, 4, 5, 6, or 7; or substituents on two different atoms are connected to form a ring of size 3, 4, 5, 6, or 7; and Z is selected from $CO_2H$, $CO_2R_9$, where $R_9$ is $C_1$, $C_2$, $C_3$, $C_4$, $C_5$ or $C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2N$-alkyl, $CONHS(O)_2N$-cycloalkyl, $CONHS(O)_2N$-heteroalkyl, $CONHS(O)_2N$-aryl, $CONHS(O)_2N$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

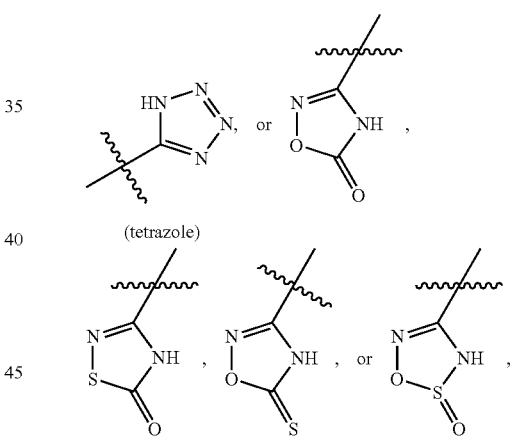

(tetrazole)

provided that when m is zero, X is absent.

In one embodiment, Z is a sulfonamide. Sulfonamides include acyl sulfonamides. For example, Z can have the formula

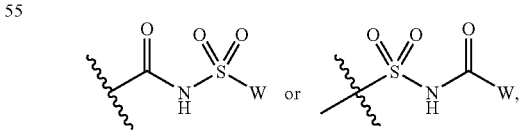

where W is a substituent is chosen to modulate the effects of the polar surface area of the Z moiety. For example, such effects include the level of oral absorption, CNS penetration, and/or rate of excretion into urine or bile. Examples of useful W substituents for this purpose include an alkyl group (optionally containing a double or triple bond), a cycloalkyl group (optionally containing a double bond), a heterocyclyl group, an aryl group or a heteroaryl group, both optionally substituted, such as those shown below:

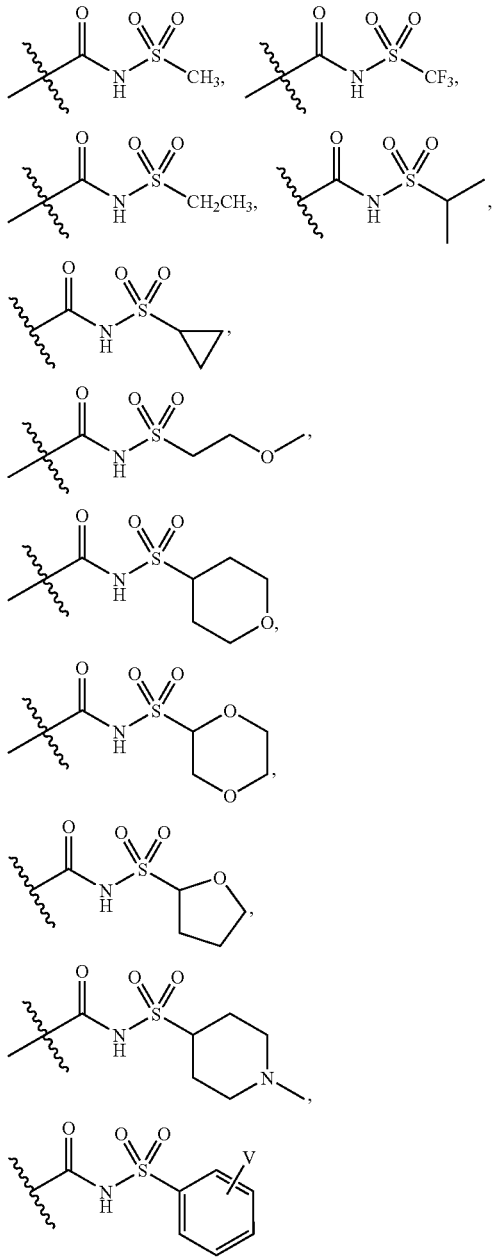

(where V is at least one side chains selected to modulate the pKa of the acylsulfonamide moiety, or to affect the physical or metabolic properties of the compound. Examples of V side chains include halogens such as F, Cl, or Br; $C_1, C_2, C_3, C_4, C_5$ or $C_6$ alkoxy groups such as $OCH_3$ or $OCH_2CH_3$; $C_1, C_2, C_3, C_4, C_5$ or $C_6$ alkyl or $C_3, C_4, C_5, C_6, C_7$ or $C_8$ cycloalkyl groups such as $CH_3$ or $CF_3$, cyclopropyl; heteroatom substituted $C_1, C_2, C_3, C_4, C_5$ or $C_6$ alkyl or $C_3, C_4, C_5, C_6, C_7$, or $C_8$ cycloalkyl, such as $CH_2OCH_3$, or $CH_2OCH_2CH_3$; electron withdrawing groups such as CN, a ketone, an amide, or a sulfone.

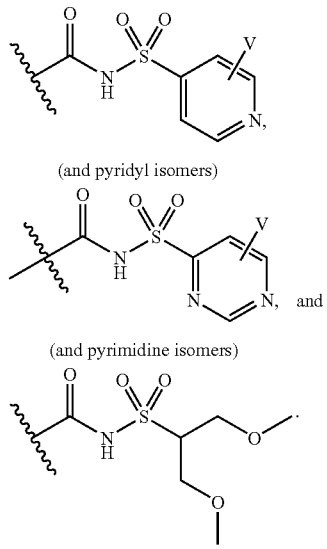

(and pyridyl isomers)

and (and pyrimidine isomers)

In one embodiment, Z is a sulfamide. Sulfamides include acyl sulfamides. For example, Z can have the formula

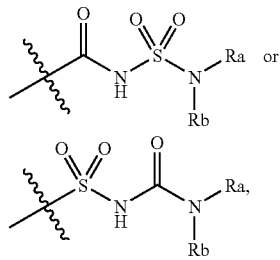

where Ra and Rb are, independently, for example an alkyl group, a cycloalkyl group, a heterocyclyl group, an aryl group or a heteroaryl group, optionally substituted. Examples include the following:

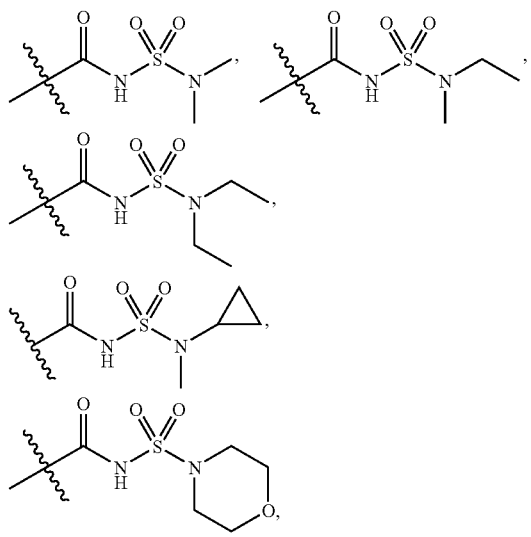

-continued

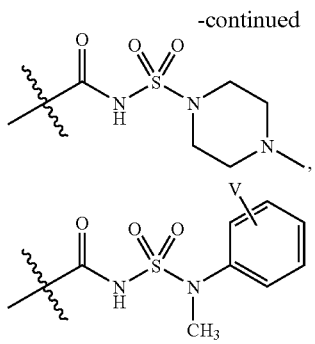

(where V is a halogen such as F, Cl, or Br; $C_1$, $C_2$, $C_3$, $C_4$, $C_5$ or $C_6$ alkoxy such as $OCH_3$ or $OCH_2CH_3$; $C_1$, $C_2$, $C_3$, $C_4$, $C_5$, or $C_6$ alkyl or $C_3$, $C_4$, $C_5$, $C_6$, $C_7$ or $C_8$ cycloalkyl such as $CH_3$ or $CF_3$, cyclopropyl; heteroatom substituted $C_1$, $C_2$, $C_3$, $C_4$, $C_5$, or $C_6$ alkyl or $C_3$, $C_4$, $C_5$, $C_6$, $C_7$ or $C_8$ cycloalkyl, such as $CH_2OCH_3$, or $CH_2OCH_2CH_3$; an electron withdrawing group such as CN, a ketone, an amide, or a sulfone),

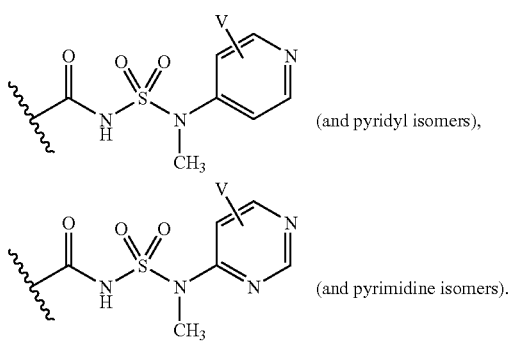

In one embodiment, Z is $CO_2H$ or tetrazole.

In one embodiment, Z is a sulfonamide or sulfamide.

In another embodiment, Z is an acyl sulfonamide. Sulfonamide can be e.g., an acyl sulfonamide such as —$CONHSO_2$-alkyl, where alkyl is $C_1$-$C_6$ straight chain alkyl, $C_3$-$C_6$ branched alkyl or $C_3$-$C_8$ cycloalkyl.

In one embodiment, at least one of $R_1$-$R_4$, $R_5$-$R_6$ and at least one of $R_7$-$R_8$ are not hydrogen.

In one embodiment, at least one of $R_2$ and $R_3$ is not H.

In another embodiment, $R_1$ is not H.

In another embodiment, $R_2$ is not H.

In another embodiment, $R_3$ is not H.

In another embodiment, $R_4$ is not H.

In another embodiment $R_1$ is F, Cl, Br, I, or $C_1$, $C_2$, $C_3$, $C_4$, $C_5$, or $C_6$ alkoxy.

In another embodiment $R_2$ is F, Cl, Br, I, or $C_1$, $C_2$, $C_3$, $C_4$, $C_5$, or $C_6$ alkoxy.

In another embodiment $R_3$ is F, Cl, Br, I, or $C_1$, $C_2$, $C_3$, $C_4$, $C_5$, or $C_6$ alkoxy.

In another embodiment $R_5$ is F, Cl, Br, I, or $C_1$, $C_2$, $C_3$, $C_4$, $C_5$, or $C_6$ alkoxy.

In one embodiment, when Z is tetrazole, at least one of $R_5$-$R_6$, and $R_7$-$R_8$ is not hydrogen.

In one embodiment, at least two of $R_1$-$R_4$ are not hydrogen.

In one embodiment, at least three of $R_1$-$R_4$ are not hydrogen.

In one embodiment, X and Y are absent.

In one embodiment, $R_5$ and $R_6$ and the carbon to which they are attached are absent.

In one embodiment, q=0.

In one embodiment, m+n+o+p=1, 2, or 3.

In one embodiment, $R_9$ is not $C_1$-$C_6$ alkyl. In another embodiment, $R_9$ is not $C_2$ alkyl.

In another embodiment, $R_1$-$R_4$ are each hydrogen.

In one embodiment, $R_5$ and $R_6$ are each methyl. In another embodiment, $R_5$ and $R_6$ are each ethyl. In one embodiment, $R_7$ and $R_8$ are each methyl. In another embodiment, $R_7$ and $R_8$ are each ethyl. In one embodiment, $R_5$ and $R_6$ and the carbon to which they are attached are connected to form a spiro ring of size 3-7. For example, in one embodiment, $R_5$ and $R_6$ and the carbon to which they are attached are connected to form a three-membered spiro (cyclopropyl) ring.

In one embodiment, the $R_5$ and $R_6$ and the carbon they are attached to are absent. In one embodiment, $R_7$ and $R_8$, together with the carbon to which they are attached, are connected to form a spiro ring of size 3 to 7. For example, $R_7$ and $R_8$ together with the carbon to which they are attached, are connected to form a spiro 3-membered cyclopropyl ring.

In one aspect, a composition of Formula I also includes a pharmaceutically acceptable excipient. In another aspect, the invention relates to a pharmaceutical composition comprising a compound of Formula I.

In another aspect, the invention provides a compound of Formula II:

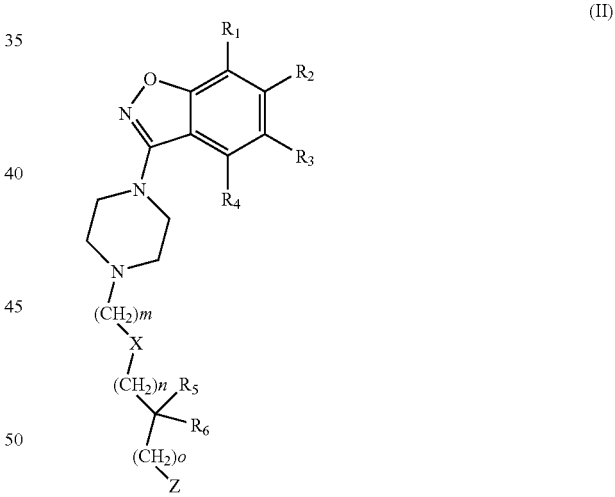

(II)

or a pharmaceutically effective salt thereof, wherein m, n, and o are, individually, 0, 1, 2, 3, 4, 5, or 6; X is absent, O, S, C(O), SO or $SO_2$; $R_1$, $R_2$, $R_3$, and $R_4$ are, independently selected from H, F, Cl, Br, $CF_3$, $CH_3$, $CH_2CH_3$, $CH(CH_3)_2$, cyclopropyl, $OCH_3$, $OCF_3$, $CH_2OCH_3$ and $CH_2OCH_2CH_3$; $R_5$, and $R_6$, are, independently, H, $C_1$-$C_5$ straight chain alkyl; $C_3$-$C_6$ branched alkyl, or $R_5$ and $R_6$ together with the carbon to which they are attached, are connected to form a spiro ring of size 3 to 7; and Z is COOH, $COOR_9$, where $R_9$ is $C_1$-$C_6$ alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2N$-alkyl;

CONHS(O)$_2$N-heteroalkyl; CONHS(O)$_2$N-aryl; CONHS(O)$_2$N-heteroaryl; or tetrazole, provided that when m is zero, X is absent.

In one embodiment, R$_5$ and R$_6$, are each methyl. In another embodiment, R$_5$ and R$_6$, are each ethyl.

In one embodiment, R$_5$ and R$_6$, together with the carbon to which they are attached, are connected to form a spiro ring of size 3 to 7. For example, in one embodiment, R$_5$ and R$_6$, together with the carbon to which they are attached, are connected to form a spiro cyclopropyl ring.

In one embodiment, Z is sulfonamide, e.g., an acyl sulfonamide. One example of an acyl sulfonamide is C(O)NHSO$_2$-alkyl; where alkyl is a C$_1$, C$_2$, C$_3$, C$_4$, C$_5$, or C$_6$ straight chain alkyl, or a C$_3$, C$_4$, C$_5$, or C$_6$ branched alkyl.

In one embodiment, Z is CO$_2$H or tetrazole.

In one embodiment, o is zero.

In one embodiment, at least one of R$_1$-R$_4$ and at least one of R$_5$-R$_6$, are not hydrogen.

In one embodiment, at least two of R$_1$-R$_4$ are not hydrogen.

In one embodiment, at least three of R$_1$-R$_4$ are not hydrogen.

In one embodiment, R$_1$ is not hydrogen. In one embodiment, R$_2$ is not hydrogen. In one embodiment, R$_3$ is not hydrogen. In one embodiment, R$_4$ is not hydrogen.

In one embodiment, X is absent.

In one embodiment, m+n=1, 2, or 3. In one aspect, a composition of Formula II also includes a pharmaceutically acceptable excipient. In another aspect, the invention relates to a pharmaceutical composition comprising a compound of Formula II.

In another aspect, the invention provides a compound of Formula III:

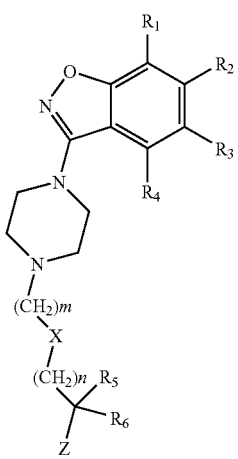

(III)

or a pharmaceutically effective salt thereof, wherein m and n are, individually, 0, 1, 2, 3, or 4, X is absent, O, S, C(O), SO or SO$_2$; R$_1$, R$_2$, R$_3$, and R$_4$ are, independently, selected from H, F, Cl, Br, CF$_3$, CH$_3$, CH$_2$CH$_3$, CH(CH$_3$)$_2$, cyclopropyl, OCH$_3$, OCF$_3$, CH$_2$OCH$_3$, and CH$_2$OCH$_2$CH$_3$; R$_5$, and R$_6$, are, independently, H, C$_1$-C$_5$ straight chain alkyl; C$_3$-C$_6$ branched alkyl, or R$_5$, and R$_6$, together with the carbon to which they are attached, are connected to form a spiro ring of size 3-7; and Z is selected from CO$_2$H, CONHS(O)$_2$-alkyl, CONHS(O)$_2$-cycloalkyl, CONHS(O)$_2$-heteroalkyl, CONHS(O)$_2$-aryl, CONHS(O)$_2$-heteroaryl, and tetrazole; provided that when m is zero, X is absent.

In one embodiment, R$_5$ and R$_6$, together with the carbon to which they are attached, are connected to form a spiro ring of size 3-7. For example, in one embodiment, R$_5$ and R$_6$, together with the carbon to which they are attached, are connected to form a spiro cyclopropyl ring.

In one embodiment, Z is CO$_2$H or tetrazole. In one embodiment, at least one of R$_1$-R$_4$, and at least one of R$_5$-R$_6$, are not hydrogen.

In another embodiment, Z is sulfonamide, e.g., an acyl sulfonamide. One example of an acyl sulfonamide is C(O)NHSO$_2$-alkyl, where alkyl is a C$_1$, C$_2$, C$_3$, C$_4$, C$_5$, or C$_6$ straight chain alkyl or a C$_3$, C$_4$, C$_5$ or C$_6$ branched alkyl.

In one embodiment, at least one of R$_1$-R$_4$ is not hydrogen.

In one embodiment, at least two of R$_1$-R$_4$ are not hydrogen.

In one embodiment, at least three of R$_1$-R$_4$ are not hydrogen.

In one embodiment, R$_5$ and R$_6$ are each methyl. In another embodiment, R$_5$ and R$_6$ are each ethyl.

In one embodiment, X is absent.

In one embodiment, m+n=1, 2, 3, or 4.

In one aspect, a composition of Formula III also includes a pharmaceutically acceptable excipient. In another aspect, the invention relates to a pharmaceutical composition comprising a compound of Formula III.

In another aspect, the invention provides a compound of Formula IV:

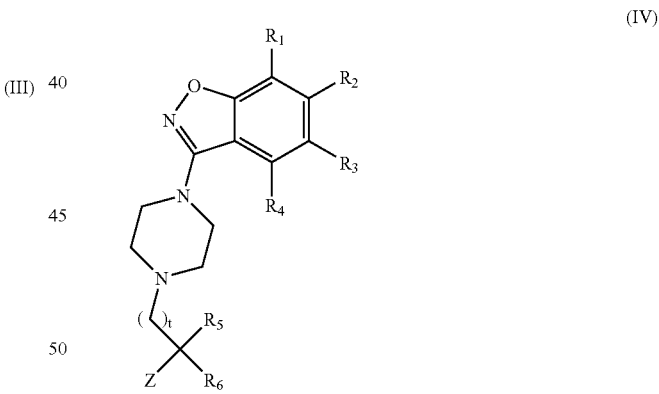

(IV)

or a pharmaceutically effective salt thereof wherein t is 1, 2, 3, 4, 5, or 6; R$_1$, R$_2$, R$_3$, and R$_4$ are, independently, H, F, Cl, Br, CF$_3$, CH$_3$, OH, OCH$_3$, CH$_2$OCH$_3$, or CH$_2$OCH$_2$CH$_3$; R$_5$-R$_6$ are H, CH$_3$, CH$_2$CH$_3$, or R$_5$ and R$_6$, together with the carbon to which they are attached, are connected to form a spiro ring of size 3 to 7; and Z is selected from CO$_2$H, CONHS(O)$_2$-alkyl, CONHS(O)$_2$-cycloalkyl, CONHS(O)$_2$-heteroalkyl, and tetrazole. In one aspect, a composition of Formula IV also includes a pharmaceutically acceptable excipient. In another aspect, the invention relates to a pharmaceutical composition comprising a compound of Formula IV.

In one embodiment, the compound of Formula IV is IVa, IVb, IVc, or IVd. For example, when R$_5$ and R$_6$ are methyl, compounds have the general formula IVa:

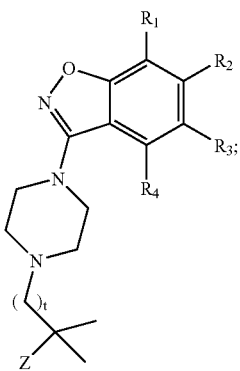

(IVa)

when $R_5$ and $R_6$ are connected to form a 3 membered Spiro ring (cyclopropyl), compounds have the general formula IVb:

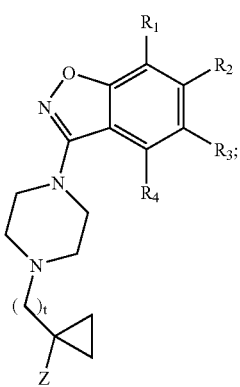

(IVb)

when $R_5$ and $R_6$ are ethyl, compounds have the general formula IVc:

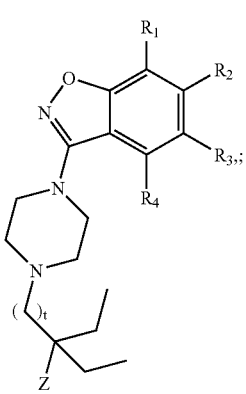

(IVc)

when $R_5$ and $R_6$ are ethyl, and the C1 carbons are connected to form a 3 membered spiro ring (cyclopropyl), compounds have the general formula IVd:

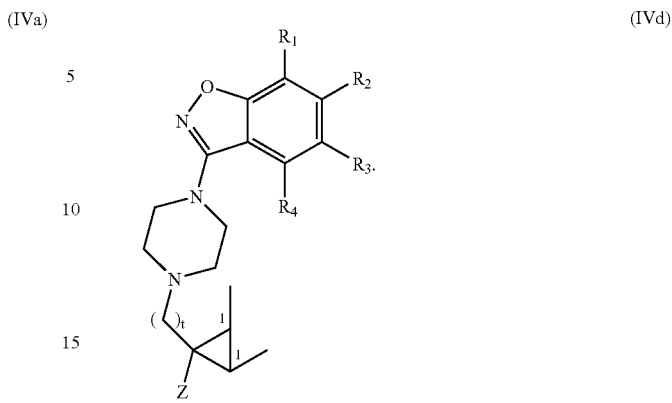

(IVd)

In one embodiment, Z is $CO_2H$ or tetrazole. In another embodiment, Z is an acyl sulfonamide. For example, Z is $CONHSO_2$-alkyl, wherein alkyl is $C_2$, $C_3$, $C_4$, $C_5$ or $C_6$ straight chain alkyl, $C_3$, $C_4$, $C_5$ or $C_6$ branched alkyl, or $C_1$, $C_2$, $C_3$, $C_4$, $C_5$, $C_6$, $C_7$, or $C_8$ cycloalkyl. In one embodiment, t is 1.

In one embodiment, at least one of $R_1$-$R_4$ and at least one of $R_5$-$R_6$, are not hydrogen.

In one aspect, the invention provides a compound having the structure of compound 1:

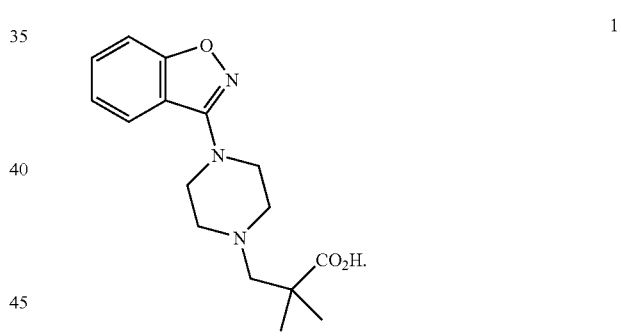

1

Representative compounds of the invention are show below.

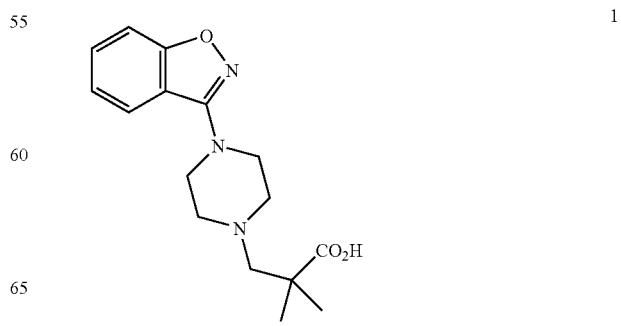

1

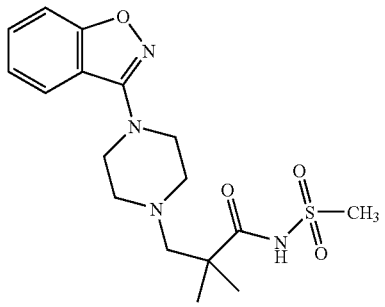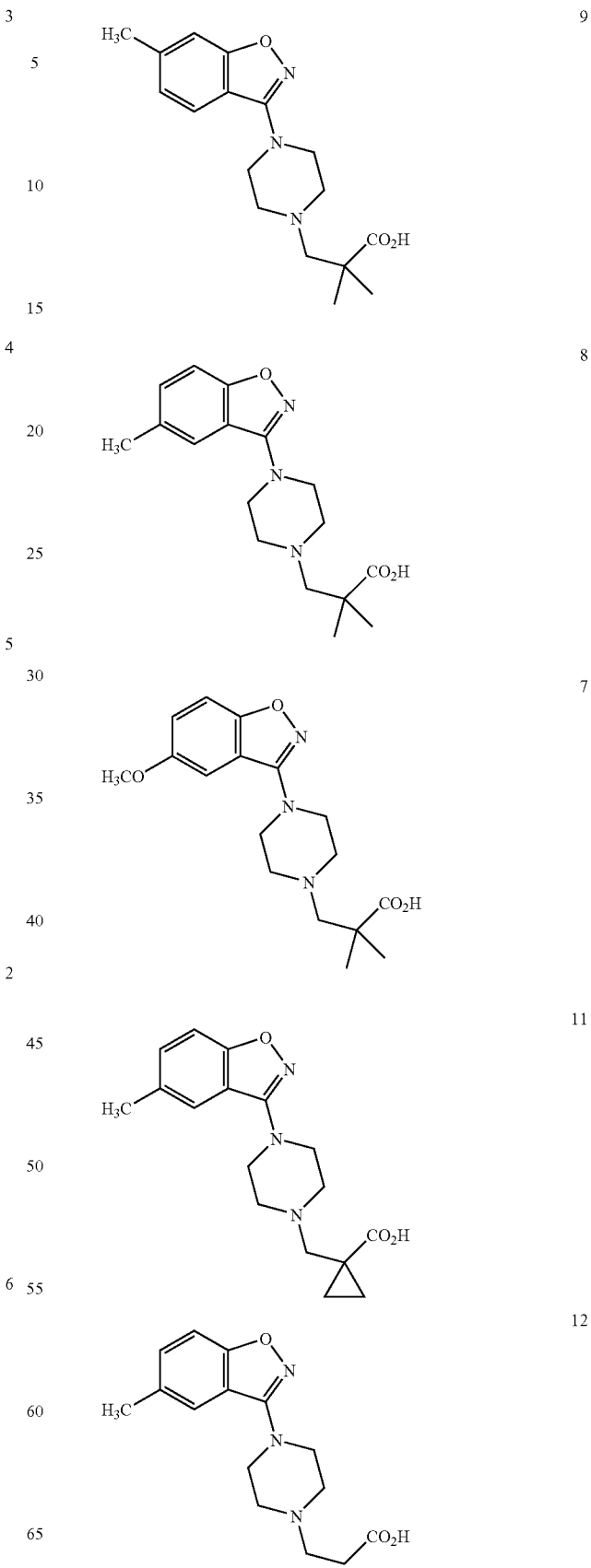

-continued

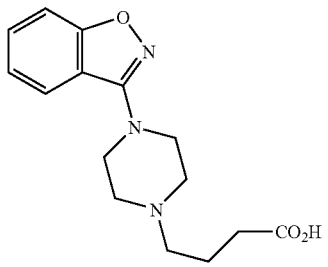
10

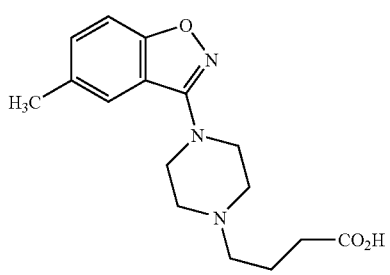
13

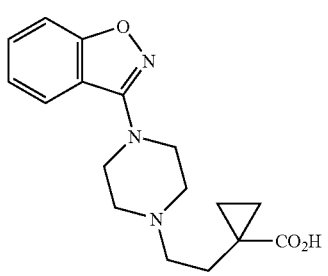
14

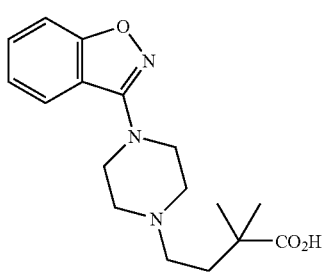
15

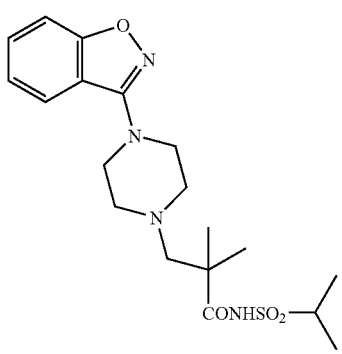
16

-continued

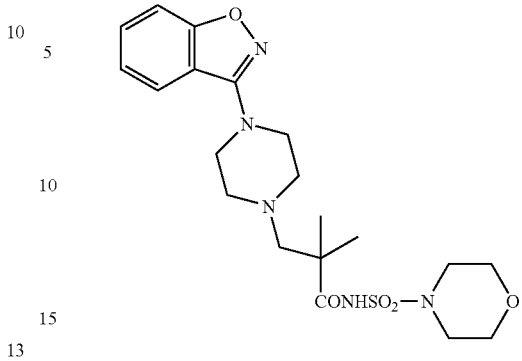
17

The compounds of the invention display binding activity to a variety of targets, including the 5HT2a receptor. Therefore, these compounds may be useful in treating or preventing diseases or disorders that implicate the 5HT2a receptor.

The compounds of the invention are used to treat a variety of subjects, including, for example, humans, companion animals, farm animals, laboratory animals and wild animals.

In one embodiment, the compounds of the invention may be useful in modulating sleep in a subject. For example, the compound may be used in decreasing the time to sleep onset, increasing the average sleep bout length, and/or increasing the maximum sleep bout length. In one embodiment, the sleep modulation may treat a sleep disorder.

In one aspect, the benzisoxazole compounds of the invention may be used in the treatment of a sleep disorder, including, for example, circadian rhythm abnormality, insomnia, parasomnia, sleep apnea syndrome, narcolepsy and hypersomnia.

In one embodiment, the benzisoxazole compounds of the invention may be used in the treatment of a circadian rhythm abnormality, such as, for example, jet lag, shift-work disorders, delayed sleep phase syndrome, advanced sleep phase syndrome and non-24 hour sleep-wake disorder.

In another embodiment, the benzisoxazole compounds can be used in the treatment of insomnia, including, for example, extrinsic insomnia, psychophysiologic insomnia, altitude insomnia, restless leg syndrome, periodic limb movement disorder, medication-dependent insomnia, drug-dependent insomnia, alcohol-dependent insomnia and insomnia associated with mental disorders, such as anxiety. The compounds of the invention may also be used to treat sleep fragmentation associated with Parkinson's disease, Alzheimer's disease, Huntington's disease, and other dystonias.

In one embodiment, the benzisoxazole compounds of the invention can be used to treat a parasomnia disorder, such as, e.g., somnambulism, pavor nocturnus, REM sleep behavior disorder, sleep bruxism and sleep enuresis.

In another embodiment, the benzisoxazole compounds can be used to treat a sleep apnea disorder, such as, for example, central sleep apnea, obstructive sleep apnea and mixed sleep apnea.

In another embodiment, the benzisoxazole compounds can be used to treat disorders related to sleep disorders, such as, for example, fibromyalgia.

In another aspect, the benzisoxazole compounds can be used to promote sleep.

DEFINITIONS

For convenience, certain terms used in the specification, examples and appended claims are collected here.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain, $C_3$-$C_6$ for branched chain). In some examples, a straight chain or branched chain alkyl has four or fewer carbon atoms in its backbone. Further, cycloalkyls have from three to eight carbon atoms in their ring structure. For example, cycloalkyls have five or six carbons in the ring structure. "$C_1$-$C_6$" includes alkyl groups containing one to six carbon atoms.

The term "substituted alkyls" refers to alkyl moieties having substituents replacing a hydrogen on at least one carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. "Substituted alkyl" further includes alkyl groups that have oxygen, nitrogen, sulfur or phosphorous atoms replacing at least one hydrocarbon backbone carbon atoms.

Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing at least one hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and, for example, have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on at least one hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing at least one hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on at least one hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, for example, from one to six, carbon atoms in its backbone structure. "Lower alkenyl" and "lower alkynyl" have chain lengths of, for example, 2-5 carbon atoms.

"Acyl" includes compounds and moieties that contain the acyl radical ($CH_3CO$—) or a carbonyl group. "Substituted acyl" includes acyl groups where at least one of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing at least one hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl", or "heterocyclic group" include closed ring structures, e.g., 3- to 10-, or 4- to 7-membered rings, which include at least one heteroatoms. The term "heteroalkyl" includes alkyl groups which contain at least one heteroatom. "Heteroatom" includes atoms of any element other than carbon or hydrogen. Examples of heteroatoms include nitrogen, oxygen, sulfur and phosphorus. The term "heteroalkyl" includes cycloalkyl groups e.g., morpholine, piperidine, piperazine, etc.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at at least one positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at at least one constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). Another anionic group is a carboxylate.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

The terms "crystal polymorphs" or "polymorphs" refer to the existence of more than one crystal form for a compound, salt or solvate thereof. Crystal polymorphs of the benzisoxazole analog compounds are prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Tautomers" refers to compounds whose structures differ markedly in arrangement of atoms, but which exist in easy and rapid equilibrium. It is to be understood that compounds of Formulae I-IVd may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples include:

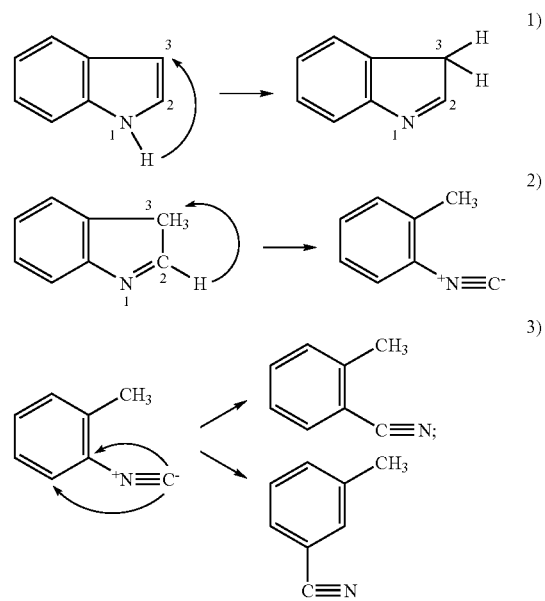

-continued

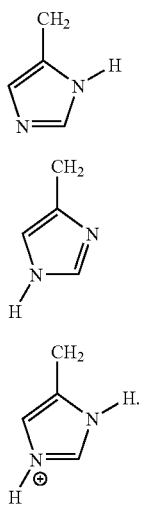

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Stable compound" and "stable structure" are meant to indicate a compound that is sufficiently robust to survive isolation to a useful degree of purity from a reaction mixture, and formulation into an efficacious therapeutic agent.

The language benzisoxazole compounds or "benzisoxazole-analog compounds" "benzisoxazole-like compounds" or "benzisoxazole derivative compounds" is intended to include analogs of benzisoxazole or compounds that include a benzene ring linked to an isozazole, (i.e., similar to that of benzisoxazole) linked to position 4 of a piperazine ring.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. For example, the reference compound can be a reference compound such as benzisoxazole, and an analog is a substance possessing a chemical structure or chemical properties similar to those of the reference benzisoxazole.

As defined herein, the term "derivative", e.g., in the term "benzisoxazole derivatives", refers to compounds that have a common core structure, and are substituted with various groups as described herein. For example, all of the compounds represented by formulae I-IVd are benzisoxazole derivatives, and have one of formulae I-IVd as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996). In some embodiments, Z is a carboxylic acid or a carboxylic acid bioisostere.

As used herein, the term "sleep disorder" includes conditions recognized by one skilled in the art as sleep disorders, for example, conditions known in the art or conditions that are proposed to be sleep disorders or discovered to be sleep disorders. A sleep disorder also arises in a subject that has other medical disorders, diseases, or injuries, or in a subject being treated with other medications or medical treatments, where the subject, as a result, has difficulty falling asleep and/or remaining asleep, or experiences unrefreshing sleep, e.g., the subject experiences sleep deprivation.

The term "treating a sleep disorder" also includes treating a sleep disorder component of other disorders, such as CNS disorders (e.g., mental or neurological disorders such as anxiety). Additionally, the term "treating a sleep disorder" includes the beneficial effect of ameliorating other symptoms associated with the disorder.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of nonREM sleep per hour.

As used herein, the term "cumulative nonREM sleep" is defined as the net total aggregate increase in the number of minutes of nonREM sleep, measured through out the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness.

As used herein, the term "sleep promotion" is defined as a decrease in the latency to sleep onset as is often, but not exclusively, measured by the Multiple Sleep Latency Test, or a decrease in the latency to return to sleep after awakening, or reduces the tendency to awaken or remain awake either spontaneously or as a response to wake-promoting ambient stimuli (e.g., noise, vibration, odor, pain, light). In general, a sleep promoting drug shortens the latency to sleep onset at desired bed time, or shortens the latency to return to sleep after night-time awakening, or may increase night-time total sleep time. A compound exhibiting these properties is said to promote sleep.

As used herein, the term "sleep consolidation" is defined as the ability to remain asleep or otherwise demonstrate persistent sleep after sleep onset, and throughout the desired sleep period, with little or no intervening wakefulness, as objectively measured by the number of night-time awakenings, sleep efficiency (number of awakenings per amount of time in bed), or number of transient arousals. In general, a sleep consolidating drug improves the ability to remain asleep by increasing the duration of continuous sleep between spontaneous episodes of wakefulness. A compound exhibiting these properties is said to consolidate sleep.

Compared with NREM sleep or wakefulness, REM sleep causes ventilatory depression and episodic cardiovascular changes. During rebound insomnia, the physiological effects of REM sleep are magnified and interrupt the normal sleep cycles.

As defined herein, "disproportionate locomotor activity inhibition" is a reduction of locomotor activity that exceeds the normal and expected reduction in behavioral activity attributable to sleep.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "pulmonary" as used herein refers to any part, tissue or organ whose primary function is gas exchange with the external environment, e.g., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" also includes a tissue or cavity that is contingent to the respiratory tract, in particular, the sinuses.

An "effective amount" of a compound of the disclosed invention is the quantity which, when administered to a subject in need of treatment, ameliorates symptoms arising from a sleep disorder, e.g., results in the subject falling asleep more rapidly, results in more refreshing sleep, reduces duration or frequency of waking during a sleep period, or reduces the duration, frequency, or intensity of other dyssomnias, parasomnias. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

A "pharmaceutically acceptable salt" or "salt" of the disclosed compound is a product of the disclosed compound that contains an ionic bond, and is typically produced by reacting the disclosed compound with either an acid or a base, suitable for administering to a subject.

A "pharmaceutical composition" is a formulation containing the disclosed compounds in a form suitable for administration to a subject. In another embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

The invention provides a method of modulating sleep by administering an effective amount of a benzisoxazole analog of the invention, which is a moiety that is an antagonist or an inverse agonist of the 5HT2a receptor or a collection of 5HT2a receptors.

Effective sleep modulators have certain characteristics that correspond with increased efficacy and decreased side effects. These characteristics include a desired half-life in a subject, controlled onset of desired sedative effects, and minimal to no detectable effect on psychomotor or other central nervous system (CNS) side effects (e.g., memory deficits, decreased muscle tone, drooping eyelids or drowsiness).

One approach to developing an effective sleep modulator is strategically derivitizing a known compound or family of compounds with sleep modulating activity. Derivitizing may enhance at least one biological properties to allow a compound to perform in an improved manner. Examples of favorable biological properties include, but are not limited to, induction of a discrete sleep or hypnotic state, activity of the therapeutic compound for a discrete period of time, penetration through the blood brain barrier into the CNS, e.g., resulting from lipophilicity of substituents or conformational lipophilicity (i.e., lipophilicity as a result of a particular conformation, such as internal salt formation between a carboxylate anion and a protonated amine), modulation of the half-life of the therapeutic compound, an alteration of charge, an alteration of pharmacokinetics, an alteration of log P by a value of at least one, increased receptor selectivity, reduced peripheral half-life, the ability to increase dosage, increased peripheral elimination, decreased anti-muscarinic activity, decreased anti-cholinergic, and any combination thereof.

Derivitizing results in a variety of effects and alter different mechanisms of action. For example, in some circumstances, a compound containing a particular functional group, such as, e.g., an ester, carboxylic acid, or alcohol group, possesses an improved selectivity for a desired receptor versus undesired receptors when compared with a compound without this group. In other circumstances, the compound containing the particular functional group is more active as a therapeutic agent for treating sleep disorders than the corresponding compound without this group. The effect of the derivitized compound depends on the identity of the addition.

By derivitizing a compound in order to enhance favorable biological properties and decrease undesirable side effects, it is possible to implement a strategy based on potential mechanistic effects or interactions. For example, in some compounds, the presence of a carboxylic acid results in the ability to form an intramolecular ionic bond that includes the corresponding carboxylate ion, e.g., zwitterion species formation with a nitrogen atom within the compound or salt bridge formation. These interactions result in favorable biological effects such as conformational lipophilicity, i.e., increased lipophilicity as a result of a particular conformation, such as internal salt formation between a carboxylate anion and a protonated amine. Such conformational lipophilicity allows penetration through the blood brain barrier into the CNS, despite that the presence of two polar ions is generally thought to inhibit crossing of the non-polar blood-brain barrier. Another benefit of the presence of the carboxylic acid is an improved ability of the compound to bind selectively to the desired receptor.

Compounds of the invention can also be derivitized to produce prodrugs. "Prodrug" includes a precursor form of the drug which is metabolically converted in vivo to produce the active drug. The invention further contemplates the use of prodrugs which are converted in vivo to the sleep modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the sleep modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate sleep modulating compound which subsequently decomposes to yield the active sleep modulating compound. In one embodiment, the prodrug is a reduced form of a carboxylate, sulfate or sulfonate, e.g., an alcohol or thiol, which is oxidized in vivo to the sleep modulating compound. Furthermore, an anionic moiety can be esterified to a group which is actively transported in vivo, or which is selectively taken up by target organs.

In general, in another aspect, the present invention relates to the use of the compounds of Formula I-IVd to modulate sleep. In one embodiment, the compounds of Formula I-IVd modulate sleep with decreased side effects: e.g., the compounds do not inhibit REM sleep (consequently, sleep induced by these compounds may more closely resemble a person's natural sleep cycles), use of the compound does not result in rebound insomnia, and/or the compounds do not inhibit locomotor activity or adversely effect body temperature.

In one embodiment, the compounds of Formula I-IVd for use in the methods of the invention have one or more of the following characteristics: an inhibition constant ($K_i$) with regard to $5HT_{2a}$ receptor binding of less than 1 μM; a $K_i$ with regard to off target binding to an off target selected from M1, M2, M3, D1, D2, α1 and α2 that is more than 5 times greater than the $K_i$ with regard to the $5HT_{2a}$ receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I-IVd for use in the methods of the invention has one or more of the following characteristics: an inhibition constant ($K_i$) with regard to $5HT_{2a}$ receptor binding of less than 300 nM; a $K_i$ with regard to off target binding to an off target selected from M1, M2, M3, D1, D2, α1 and α2 that is more than 10 times greater than the Ki with regard to $5HT_{2a}$; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I-IVd for use in the methods of the invention has one or more of the following characteristics: an inhibition constant ($K_i$) with regard to $5HT_{2a}$ receptor binding of less than 150 nM; a $K_i$ with regard to off target binding to an off target selected from D1, D2, M1, M2, M3, α1 and α2, that is more than 20 times greater than the Ki with regard to $5HT_{2a}$; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

The in vitro selection criteria for compounds of the invention are shown in Table 1.

TABLE 1

| $5HT_{2a}$ Binding (Primary Target) | Ki <1 μMolar |
|---|---|
| Off Target Binding | |
| Cholinergic M1, M2, M3 | Ki >5 times the measured $5HT_{2a}$ receptor Ki |
| Dopamine D1, D2 | Ki >5 times the measured $5HT_{2a}$ receptor Ki |
| Adrenergic α1, α2 | Ki >5 times the measured $5HT_{2a}$ receptor Ki |

In another embodiment, the off target binding Ki is 50 times the measured $5HT_{2a}$ receptor Ki. In some embodiments, the off target binding Ki is 100 times the measured $5HT_{2a}$ receptor Ki.

In vitro binding assays are used to determine $5HT_{2a}$ binding (i.e., primary target binding) and M1, M2 and M3 binding (i.e., off target binding). These binding assays measure the ability of benzisoxazole analogs to displace known standards from the $5HT_{2a}$, M1, M2, and M3 receptors, wherein M1, M2, and M3 are cholinergic (muscarinic) receptors. Similar assays are performed with $5HT_{2a}$ and dopamine receptors (D1, and D2), and with $5HT_{2a}$ and adrenergic receptors (α1 and α2).

The binding studies against the $5HT_{2a}$ receptor indicate binding affinity, and therefore, the results of the binding assays are an indication of the activity of the benzisoxazole analog compound. The binding studies against the muscarinic receptors indicate the extent to which the compounds bind the muscarinic receptors responsible for anti-cholinergic activity of the compound. Binding to muscarinic receptors results in several undesired side effects of many known antihistamines, e.g., dry-mouth. A decrease in the binding of the compounds to the M1-M3 receptors, relative to the binding of the compound to the $5HT_{2a}$ receptor, is an indication of the greater specificity of the compound for the $5HT_{2a}$ receptor over the muscarinic receptor. Moreover, a drug with increased specificity for the $5HT_{2a}$ receptor possesses less anti-cholinergic side effects.

The $5HT_{2a}$ binding of benzisoxazole analogs of the invention (also referred to herein as "test compounds" or "compounds of the invention") is determined by measuring the specific binding of a given test compound, or series of test compounds, to the $5HT_{2a}$ receptor, and comparing it with the specific binding of known standard (i.e., reference compound).

In vitro selection criteria for benzisoxazole analogs of the invention are shown in Table 2.

TABLE 2

| $5HT_{2a}$ Binding (Primary Target) | Ki <300 nMolar |
|---|---|
| Off Target Binding | |
| Cholinergic M1, M2, M3 | Ki >10 times the measured $5HT_{2a}$ receptor Ki |
| Dopamine D1, D2 | Ki >10 times the measured $5HT_{2a}$ receptor Ki |
| Adrenergic α1, α2 | Ki >10 times the measured $5HT_{2a}$ receptor Ki |

Other in vitro selection criteria for benzisoxazole analogs of the invention are shown in Table 3.

TABLE 3

| 5HT$_{2a}$ Binding (Primary Target) | Ki <150 nMolar |
|---|---|
| Off Target Binding | |
| Cholinergic M1, M2, M3 | Ki >20 times the measured 5HT$_{2a}$ receptor |
| Dopamine D1, D2 | Ki >20 times the measured 5HT$_{2a}$ receptor |
| Adrenergic α1, α2 | Ki >20 times the measured 5HT$_{2a}$ receptor Ki |

5HT$_{2a}$ binding (primary target binding) and M1, M2 and M3 binding (off target binding) are determined using the 5HT$_{2a}$, M1, M2 and M3 binding assays described.

The M1 binding assay determines the M1 binding of a test compound by measuring the specific binding of a given test compound to M1 and comparing it with the specific binding of a reference compound. (See e.g., Buckley, et al., Mol. Pharmacol. 35:469-76 (1989) (with modifications)). Reference compounds used in the M1 binding assay include, for example, scopolamine, MethylBr (K$_i$ 0.09 nM); 4-DAMP methiodide (K$_i$ 0.27 nM); pirenzepine (K$_i$ 2.60 nM); HHSID (K$_i$ 5.00 nM); and methoctramine (K$_i$ 29.70 nM).

For example, in one embodiment of the M1 binding assay, the M1 muscarinic receptor is a human recombinant M1 expressed in CHO cells, and a radioligand, [$^3$H]-scopolamine, N-methyl chloride (80-100 Ci/mmol) at a final ligand concentration of 0.5 nM is used to detect specific binding for M1. The assay characteristics include a K$_D$ (binding affinity) of 0.05 nM and a B$_{max}$ (receptor number) of 4.2 pmol/mg protein. (−)-scopolamine, methyl-, bromide (methylscopolamine bromide) (1.0 μM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M1 binding site.

The M2 binding assay determines the M2 binding of a test compound by measuring the specific binding of a given test compound to M2 and comparing it with the specific binding of a reference compound. (See e.g., Buckley, et al., Mol. Pharmacol. 35:469-76 (1989) (with modifications)). Reference compounds used in the M2 binding assay include, for example, scopolamine, MethylBr (K$_i$ 0.3 nM); 4-DAMP methiodide (K$_i$ 20.7 nM); methoctramine (K$_i$ 20.460 nM); HHSID (K$_i$ 212.7 nM); and pirenzepine (K$_i$ 832.9 nM).

For example, in one embodiment of the M2 binding assay, the M2 muscarinic receptor is a human recombinant M2 expressed in CHO cells, and a radioligand, [$^3$H]-scopolamine, N-methyl chloride (80-100 Ci/mmol) at a final ligand concentration of 0.5 nM is used to detect specific binding for M1. The assay characteristics include a K$_D$ (binding affinity) of 0.29 nM and a B$_{max}$ (receptor number) of 2.1 pmol/mg protein. (−)-scopolamine, methyl-, bromide (methylscopolamine bromide) (1.0 μM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M2 binding site.

The M3 binding assay determines the M3 binding of a test compound by measuring the specific binding of a given test compound to M3 and comparing it with the specific binding of a reference compound. (See e.g., Buckley, et al., Mol. Pharmacol. 35:469-76 (1989) (with modifications)). Reference compounds used in the M3 binding assay include, for example, scopolamine, MethylBr (K$_i$ 0.3 nM); 4-DAMP methiodide (K$_i$ 0.8 nM); HHSID (K$_i$ 14.5 nM); pirenzepine (K$_i$ 153.3 nM); and methoctramine (K$_i$ 700.0 nM).

For example, in one embodiment of the M3 binding assay, the M3 muscarinic receptor is a human recombinant M3 expressed in CHO cells, and a radioligand, [$^3$H]-scopolamine, N-methyl chloride (80-100 Ci/mmol) at a final ligand concentration of 0.2 nM is used to detect specific binding for M1. The assay characteristics include a K$_D$ (binding affinity) of 0.14 nM and a B$_{max}$ (receptor number) of 4.0 pmol/mg protein. (−)-scopolamine, methyl-, bromide (methylscopolamine bromide) (1.0 μM) is used as the non-specific determinant, reference compound and positive control. Binding reactions are carried out in 50 mM TRIS-HCl (pH 7.4) containing 10 mM MgCl$_2$, 1 mM EDTA for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M3 binding site.

5HT2a binding is determined as described for example in British Journal of Pharmacology (1995) 115, 622-628.

Other in vitro selection criteria for benzisoxazole analogs of the invention includes HERG binding. HERG binding is determined using a hERG block comparative study to evaluate the effect of a given test compound on cloned hERG channels expressed in mammalian cells. (See e.g., Brown and Rampe, Pharmaceutical News 7:15-20 (2000); Rampe et al., FEBS Lett., 417:28-32 (1997); Weirich and Antoni, Basic Res. Cardiol. 93 Suppl. 1: 125-32 (1998); and Yap and Camm, Clin. Exp. Allergy, 29 Suppl 3, 174-81 (1999)).

Binding of hERG, the cardiac potassium channel responsible for the rapid delayed rectifier current (I$_{Kr}$) in human ventricles, is evaluated because inhibition of I$_{Kr}$ is the most common cause of cardiac action potential prolongation by non-cardiac drugs. (See Brown and Rampe (2000), Weirich and Antoni (1998); and Yap and Camm (1999)). Increased action potential duration causes prolongation of the QT interval that has been associated with a dangerous ventricular arrhythmia, torsade de pointes. (Brown and Rampe (2000)).

In the hERG assay, hERG channels are expressed in a human embryonic kidney cell line (HEK293) that lacks endogenous I$_{Kr}$. In some cases, expression in a mammalian cell line can be preferable to transient expression in Xenopus oocytes, as the latter demonstrates a consistent 10-100 fold lower sensitivity to hERG channel blockers. (See, Rampe 1997).

In one embodiment of the hERG assay, the positive control (i.e., reference compound) is terfenadine (Sigma, St. Louis Mo.), which has been shown, at a concentration of 60 nM, to block hERG current by approximately 75%. Test compounds are delivered in HEPES-buffered physiological saline (HB-PS)+0.1% dimethyl sulfoxide (DMSO). Each test compound is applied at a concentration of 10 μM to the HEK293 cells expressing hERG (n≧3, where n=the number of cells). Cells are exposed to the test compound for the time necessary to reach steady-state block, but not longer than 10 minutes. The positive control (60 mM terfenadine) is applied to two cells (n≧2).

The hERG-exposed cells are then transferred to the recording chamber and superfused with HB-PS solution. The pipette solution for whole cell recordings includes potassium aspartate (130 mM), MgCl$_2$ (5 mM), EGTA (5 mM), ATP (4 mM), and HEPES (10 mM) at a pH adjusted to 7.2 with KOH. Onset and steady state block of hERG current due to the test compound are measured using a pulse pattern with fixed amplitudes (depolarization: +20 mV for 2 seconds; repolarization: −50 mV for 2 seconds), repeated at 10 second intervals, from a holding potential of −80 mV. Peak tail current is measured during the 2 second step to −50 mV. A steady state is maintained for at least 30 seconds before applying the test compound or positive control compound. Peak tail currents are measured until a new steady state is achieved.

In addition to the in vitro selection criteria described above, compounds of the invention may be selected using the following in vivo sleep-wake and physiological assessments:

NonREM Sleep: Benzisoxazole analogs are selected if, in adult, male Wistar rats, (i) peak nonREM amount exceeds 55% nonREM per hour by no later than the third hour post-treatment; and (ii) the nature of this increase in nonREM sleep is such that the net cumulative total increase in nonREM sleep in the initial 6 hours post-treatment (adjusted for baseline at the corresponding circadian time 24 hours earlier, and relative to Vehicle control treatment) is not less than 20 minutes in total for compound doses that produces maximum sleep consolidation as measured by sleep bout length, when drug is delivered orally.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of nonREM sleep per hour.

As used herein, the term "cumulative nonREM sleep" is defined as the net total aggregate increase in the number of minutes of nonREM sleep, measured through out the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness. The following non-limiting description illustrates this concept: WWWWSSSSWSSSSSSSWWSSSSSSSWWWW, wherein each letter represents the predominant state of arousal (S=sleep, W=wake) observed each 10 seconds. The measured sleep "bout" is 21 ten-second epochs or 3.5 minutes in duration.

Sleep Consolidation: Benzisoxazole analogs are selected if, in adult male Wistar rats, (i) the absolute duration of longest continuous sleep episodes (i.e., "sleep bout") post-treatment is greater than 13 minutes in duration; (ii) the net longest sleep bout post treatment is greater than or equal to 3 minutes when adjusted for baseline 24 hours earlier and calculated relative to vehicle treatment; and (iii) the mean absolute duration of every sleep bout when averaged per hour, on an hour by hour basis, is greater than or equal to 5 minutes. The aforementioned selection criteria assume that stages of sleep and wakefulness are determined continuously every 10 seconds (e.g., 10 second sleep scoring "epochs"), that sleep and wakefulness are measured polygraphically using EEG and EMG criteria, and sleep episodes (comprised of nonREM and/or REM sleep) are defined as continuous "bouts" until the episode is interrupted by greater than two contiguous 10 second epochs of wakefulness.

As used herein, the term "longest sleep bout length" is defined as the total number of minutes an animal remains asleep (nonREM and/or REM sleep stages) during the single longest sleep bout that occurred beginning in a given hour post-treatment. The "sleep bout length" measurement criteria assumes sleep is measured continuously in 10 second epochs, and is scored based upon the predominant state, computed or otherwise determined as a discrete sleep stage (where sleep stages are defined as nonREM sleep, REM sleep, or wakefulness) during the 10 second interval that defines the epoch.

The term "average sleep bout length" is defined as the average duration (in minutes) of every and all sleep episodes or bouts that began in a given hour, independent of the individual duration of each episode or bout.

Concurrently Measured Side Effects: Benzisoxazole analogs are selected if, in adult, male Wistar rats, these compounds (i) do not produce appreciable amounts of rebound insomnia; (ii) do not appreciably inhibit REM sleep; and (iii) do not disproportionately inhibit locomotor motor activity and/or motor tone relative to the normal effects of sleep itself. The threshold definitions for these three side-effect variables are as follows:

"Rebound insomnia" is defined as period of rebound, paradoxical, or compensatory wakefulness that occurs after the sleep promoting effects of a hypnotic or soporific agent. Rebound insomnia is typically observed during the usual circadian rest phase 6-18 hours post-treatment at CT-18 (6 hours after lights-off, given LD 12:12), but can occur at any time during the initial 30 hours post-treatment. Rebound is considered unacceptable when, in the adult, male Wistar rat, excess cumulative wakefulness associated with rebound insomnia is greater than 10% reduction in average of hourly NonREM sleep times during post-treatment circadian rest phase (lights-on).

In adult, male Wistar rats, rebound insomnia manifests as an increase in wakefulness relative to corresponding times at baseline (24 hours earlier) subsequent to a drug-induced sleep effect, and rebound insomnia is measured cumulatively.

"REM sleep inhibition" is defined as the reduction of REM sleep time post-treatment at CT-18 (6 hours after lights-off; LD 12:12) or at CT-5 (5 hours after lights-on; LD 12:12). Compounds that reduce REM sleep time by greater than 15 minutes (relative to baseline and adjusted for vehicle treatment) when administered at either CT-18 or CT-5 are considered unacceptable.

As defined herein, "disproportionate locomotor activity inhibition" is a reduction of locomotor activity that exceeds the normal and expected reduction in behavioral activity attributable to sleep. Logic dictates that if an animal is asleep, there will normally be a corresponding reduction in locomotor activity. If a hypnotic or soporific compound reduces locomotor activity levels in excess of 20% greater than that explained by sleep alone, the compound is deemed unacceptable. Locomotor activity (LMA) or motor tone may be quantified objectively using any form of behavioral locomotor activity monitor (non-specific movements, telemetry-based activity monitoring, 3-dimensional movement detection devices, wheel running activity, exploratory measures, electromyographic recording, etc.) so long as it is measured concurrently with objective sleep-wakefulness measures in the same animal.

In one embodiment, locomotor activity within the animal's cage is measured using a biotelemetry device surgically implanted in the animal's peritoneal cavity; the implantable device and associated telemetry receiver detects if and how much animal moves within the cage. Sleep and wakefulness is measured in 10 second epochs simultaneously. Counts of locomotor activity per unit time are divided by the concurrent amount of wakefulness per the same unit, yielding a "locomotor activity intensity" (LMAI) measure for that unit time. Hypnotic or soporific compounds administered at CT-18 (6 hours after lights-off; LD 12:12) that decrease locomotor activity per unit time awake by greater than 20% relative to vehicle would be judged unacceptable.

In another embodiment, the benzisoxazole analogs of the invention are selected using the in vivo sleep-wake and physiological assessment criteria shown in Table 4:

TABLE 4

| SCORE-2000 | Absolute Value | Change from baseline value relative to vehicle only |
|---|---|---|
| NonREM Peak Time | >55% sleep/hour peak | Not applicable |
| Cumulative NonREM | Not applicable | >20 minutes at ED100 for MSBL at $T_{1-6}$ |
| Longest Sleep Bout | >17 minutes absolute peak | >5 minutes |
| Average Sleep Bout | >6 minutes absolute peak | Not used in SAR cuts |
| Rebound Insomnia | <20% reduction in average of hourly NonREM sleep times during post-treatment circadian rest phase (lights-on) | Not applicable |
| REM Sleep Inhibition | not applicable | not to exceed 15 minutes, Rx at CT5 |
| LMAI | not applicable | not to exceed 20% LMAI reduction |

Methods for evaluating these sleep-wake and physiological assessment criteria are described above. The "absolute value" shown in second column of Table 4 refers to the value as determined for each test compound, while the "change" value shown in the third column of Table 4 reflects an adjusted value in which the absolute value is the difference from vehicle, when the vehicle values are adjusted for baseline.

In some embodiments, the longest sleep bout is greater than 13 minutes in duration. In others, it is greater than 17 minutes in duration. In some embodiments, the net longest sleep bout post treatment is greater than or equal to 3 minutes in duration. In others, it is greater than or equal to 6 minutes in duration.

Other in vivo sleep-wake and physiological assessment criteria used to select benzisoxazole analogs of the invention include measurement of acute body temperature and latent body temperature as a change in baseline relative to vehicle. The acute body temperature change should not exceed $-0.60°$ C., and the latent body temperature change should not exceed $+0.60°$ C. at Time 1-6 hours. The acute body temperature ($T_{1-6}$) is adjusted for the corresponding baseline measured 24 hours earlier, relative to vehicle (the decrease from vehicle). The latent body temperature, measured 7-18 hours post drug treatment ($T_{7-18}$), is adjusted for the corresponding baseline measured 24 hours earlier, relative to vehicle (the decrease from vehicle).

The compounds, or pharmaceutically acceptable salts thereof, is administered orally, nasally, transdermally, pulmonary, inhalationally, buccally, sublingually, intraperintoneally, intravenously, rectally, intrapleurally, intrathecally and parenterally. In another embodiment, the compound is administered orally. One skilled in the art will recognize the advantages of certain routes of administration.

In some embodiments, a compound of Formula I-IVd is administered as a pharmaceutically acceptable salt. One skilled in the art will recognize the various methods for creating pharmaceutically acceptable salts and identifying the appropriate salt. In another embodiment, the compound or pharmaceutically acceptable salt thereof is included in a pharmaceutical composition.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

A subject in need of treatment has a disease or disorder that can affect the subject's health and/or wellbeing.

For example, the disorder can be a sleep disorder. It is well known in the art that certain medical disorders, for example, central nervous system (CNS) disorders, e.g. mental or neurological disorders, e.g., anxiety, can have a sleep disorder component, e.g., sleep deprivation. Thus, "treating a sleep disorder" also includes treating a sleep disorder component of other disorders, e.g., CNS disorders. Further, treating the sleep disorder component of CNS disorders can also have the beneficial effect of ameliorating other symptoms associated with the disorder. For example, in some subjects experiencing anxiety coupled with sleep deprivation, treating the sleep deprivation component also treats the anxiety component. Thus, the present invention also includes a method of treating such medical disorders.

For example, sleep disorders associated with mental disorders include psychoses, mood disorders, anxiety disorders, panic disorder, addictions, and the like. Specific mental disorders include, for example, depression, obsessive compulsive disorder, affective neurosis/disorder, depressive neurosis/disorder, anxiety neurosis; dysthymic disorder, behavior disorder, mood disorder, schizophrenia, manic depression, delirium, and alcoholism.

Sleep disorders associated with neurological disorders include, for example, cerebral degenerative disorders, dementia, parkinsonism, Huntington's disease, Alzheimer's, fatal familial insomnia, sleep related epilepsy, electrical status epilepticus of sleep, and sleep-related headaches. Sleep disorders associated with other medical disorders include, for example, sleeping sickness, nocturnal cardiac ischemia, chronic obstructive pulmonary disease, sleep-related asthma, sleep-related gastroesophageal reflux, peptic ulcer disease, and fibrositis syndrome.

In some circumstances, sleep disorders are also associated with pain, e.g., neuropathic pain associated with restless leg syndrome; migraine; hyperalgesia, fibromyalgia, pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labor pain; cancer pain; post-chemotherapy pain; post-stroke pain; post-operative pain; neuralgia; conditions associated with visceral pain including irritable bowel syndrome, migraine and angina.

Other sleep disorders include, for example, short sleeper, long sleeper, subwakefulness syndrome, fragmentary myoclonus, sleep hyperhidrosis, menstrual-associated sleep disorder, pregnancy-associated sleep disorder, terrifying hypnagogic hallucinations, sleep-related neurogenic tachypnea, sleep-related laryngospasm, and sleep choking syndrome.

Insomnia is typically classed into sleep onset insomnia, where a subject takes more than 30 minutes to fall asleep; and sleep maintenance insomnia, where the subject spends more than 30 minutes awake during an expected sleep period, or, for example, waking before the desired wake-up time with difficulty or an inability to get back to sleep. The disclosed compounds are particularly effective in treating sleep onset and sleep maintenance insomnias, insomnia resulting from circadian rhythm adjustment disorders, or insomnia resulting from CNS disorders. One embodiment is treating a subject for a circadian rhythm adjustment disorder. Another embodiment is treating a subject for insomnia resulting from a mood disorder. In other embodiments, a subject is treated for sleep apnea, somnambulism, night terrors, restless leg syndrome, sleep onset insomnia, and sleep maintenance insomnia. For example, a subject is treated for sleep onset insomnia or sleep maintenance insomnia. The disclosed compounds are effective for treating sleep onset insomnia. The disclosed compounds are also effective for treating sleep maintenance insomnia. In one embodiment, the disclosed compounds improve the quality of sleep e.g., the amount of slow wave sleep is increased.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to treat, prevent, counter or arrest the progress of the condition.

Oral dosages in humans of the present invention, when used for the indicated effects, will range between about 0.05 to 5000 mg/day orally. Effective amounts of the disclosed compounds typically range between about 0.01 mg per day and about 100 mg per day, and between about 0.1 mg per day and about 10 mg/day. Techniques for administration of the disclosed compounds of the invention can be found in *Remington: the Science and Practice of Pharmacy*, 19$^{th}$ edition, Mack Publishing Co., Easton, Pa. (1995).

For example, in some embodiments, an acid salt of a compound containing an amine or other basic group is obtained by reacting the compound with a suitable organic or inorganic acid, such as hydrogen chloride, hydrogen bromide, acetic acid, perchloric acid and the like. Compounds with a quaternary ammonium group also contain a counter anion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid.

Salts of compounds containing a carboxylic acid or other acidic functional group are prepared by reacting with a suitable base. Such a pharmaceutically acceptable salt is made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-3-phenethylamine, dehydroabietylamine, N,N'-bisdehydroabietylamine, glucamine, N-methylglucamine, collidine, quinine, quinoline, and basic amino acid such as lysine and arginine.

In some embodiments, certain compounds and their salts also exist in the form of solvates, for example hydrates, and the present invention includes each solvate and mixtures thereof.

The disclosed compounds, and salts or solvates thereof may exist in more than one crystal form, e.g., as "crystal polymorphs" or "polymorphs". Crystal polymorphs of the disclosed compounds are prepared by crystallization under different conditions. For example, using different solvents or different solvent mixtures for recrystallization; crystallization at different temperatures; various modes of cooling, ranging from very fast to very slow cooling during crystallization, and the like. Polymorphs are also obtained by heating or melting the disclosed compounds followed by gradual or fast cooling. The presence of polymorphs is determined by solid probe nuclear magnetic resonance spectroscopy, infrared spectroscopy, differential scanning calorimetry, powder X-ray diffraction, and other techniques known to one skilled in the art.

In an embodiment, the compounds described herein, and the pharmaceutically acceptable salts thereof are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the disclosed compounds of the invention can be found in *Remington: the Science and Practice of Pharmacy*, above.

Typically, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, or polymorphs thereof, can be combined with sterile aqueous or organic media to form injectable solutions or suspensions. Injectable compositions are, for example, aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, for example about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to useful to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, for example about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, for example less than about ninety seconds. Further, some embodiments of the present invention are formulated as compositions that release their active ingredients in less than about thirty seconds, for example, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The benzisoxazole analogs of the invention are also formulated as "pulsed release" formulations, in which the analog is released from the pharmaceutical compositions in a series of releases (i.e., pulses). The benzisoxazole analogs are also formulated as "sustained release" formulations in which the analog is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose). For example, polyanionic β-cyclodextrin derivatives with a sodium sulfonate salt group separate from the lipophilic cavity by an alkyl ether spacer group or polysaccharides. In an embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10.5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

In addition to the therapeutic formulations described above, a therapy including the compounds of the present invention optionally includes, co-administration with at least one additional therapies, e.g., drugs or physical or behavioral treatments (e.g., light therapy, electrical stimulation, behavior modification, cognitive therapy, circadian rhythm modification, and the like). Such a practice is referred to as "combination therapy." The other therapy or therapies in the combination therapy include therapies recognized by one skilled in the art as desirable in combination with the compound of the invention, for example, therapies known to the art or therapies which are proposed or discovered in the art for treating sleep disorders or treating diseases associated with sleep disorders, for example, therapies for any of the sleep disorders or other conditions disclosed herein. In some embodiments the compound is administered as a combination therapy whereas it is administered as a monotherapy in other embodiments.

Typically, the compound is administered as a monotherapy.

One skilled in the art will appreciate that a therapy administered in combination with the compounds of the present invention is directed to the same or a different disorder target as that being targeted by the compounds of the present invention. Administration of the compound of the invention is first, followed by the other therapy; or alternatively, administration of the other therapy may be first. The other therapy is any known in the art to treat, prevent, or reduce the symptoms of the targeted disorder, e.g., a sleep disorder, or other disorders, e.g., other CNS disorders. In addition, some embodiments of the present invention have compounds administered in combination with other known therapies for the target disorder. Furthermore, the other therapy includes any agent of benefit to the patient when administered in combination with the disclosed compound.

For example, in some embodiments where the other therapy is a drug, it is administered as a separate formulation or in the same formulation as the compound of the invention. A compound of the invention is administered in combination therapy with any at least one of commercially-available, over-the-counter or prescription medications, including, but not limited to antihistamines, antimicrobial agents, fungistatic agents, germicidal agents, hormones, antipyretic agents, antidiabetic agents, bronchodilators, antidiarrheal agents, antiarrhythmic agents, coronary dilation agents, glycosides, spasmolytics, antihypertensive agents, antidepressants, antianxiety agents, antipsychotic agents, other psychotherapeutic agents, steroids, corticosteroids, analgesics, cold medications, vitamins, sedatives, hypnotics, contraceptives, nonsteroidal anti-inflammatory drugs, blood glucose lowering agents, cholesterol lowering agents, anticonvulsant agents, other antiepileptic agents, immunomodulators, anticholinergics, sympatholytics, sympathomimetics, vasodilatory agents, anticoagulants, antiarrhythmics, prostaglandins having various pharmacologic activities, diuretics, sleep aids, antihistaminic agents, antineoplastic agents, oncolytic agents, antiandrogens, antimalarial agents, antileprosy agents, and various other types of drugs. For example, GABA agonists, alpha-2-delta modulators; other 5-HT2a antagonists and inverse agonists are useful in combination with the compounds of the invention for treating sleep disorders. See Goodman and Gilman's The Basis of Therapeutics (Eighth Edition, Pergamon Press, Inc., USA, 1990) and The Merck Index (Eleventh Edition, Merck & Co., Inc., USA, 1989).

Examples of drugs used in combination with the compounds of the invention include, but are not limited to, AMBIEN® STILNOX® (zolpidem tartrate), indiplon, ESTORRA™ (eszopiclone), NEURONTIN® (gabapentin), LYRICA® (pregabalin), eplivanserin, SONATA® (zaleplon), LUNESTA™ (eszopiclone), ZOPICLONE™ (imovane), DESYREL™ (trazodone hydrochloride), SEROQUEL® (quetiapine fumarate), CLOZARIL® (clozapine), ZYPREXA™ (olanzapine), RISPERDAL® (risperidone), M100907 and melatonin antagonists e.g., ROSEREM™ (ramelteon).

In one embodiment, the compounds of the invention are useful in combination with a mechanical therapy, such as CPAP. "CPAP" or "continuous positive airway pressure" is a mechanical treatment for sleep apnea and other sleep-related breathing disorders (including snoring) which is typically administered via the nose or mouth of the patient.

Under CPAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action, which prevents or lessens airway collapse and therefore, obstructive sleep apnea. Although an effective therapeutic response is observed in most patients who undergo CPAP treatment, many patients cannot tolerate the apparatus or pressure and refuse treatment. Moreover, recent covert monitoring studies demonstrated that long-term compliance with CPAP treatment is very poor. It is known that patients remove their mask while sleeping.

In one aspect, the compound of the invention is administered in conjunction with a CPAP device to promote sleep. In another aspect, the compound of the invention is administered in conjunction with a CPAP device to improve sleep. In another aspect, the compound of the invention is administered in conjunction with a CPAP device to improve compliance regarding with CPAP treatment. Without wishing to be bound by theory, it is thought that by administering an effective amount of a sleep promoting compound of the invention to a patient in conjunction with CPAP treatment, the patient will sleep better and more soundly and therefore, not be as likely to remove the mask.

In one embodiment, the compound of the present invention is administered prior to the CPAP treatment. In another embodiment, the compound of the present invention is administered at substantially the same time as the CPAP treatment. In one embodiment, parallel administration of an effective amount of the compound is accomplished by adding an additional aerosol channel to the air pressure treatment portion of the CPAP device, thus administering the compound of the present invention in a nebulized form via the nasal or oral mask of the CPAP device. Alternatively, an effective amount of the compound can be added to the water or into the liquid reservoir that is typically part of the CPAP treatment device.

Using the CPAP mask treatment, the compound of the invention is administered in a low concentration throughout the night, or at higher concentrations, as a bolus, at different time points in the beginning and during the course of the night.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLE 1

Synthesis of Benzisoxazole Compounds

A general synthesis of a benzisoxazole piperazine compound is shown in Scheme 1.

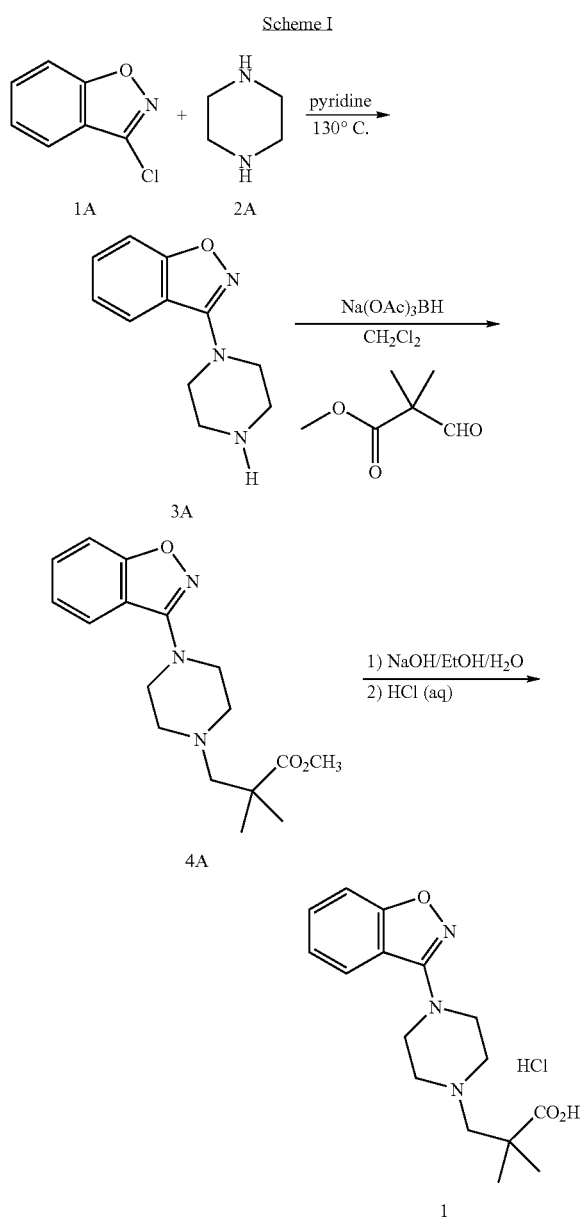

3-Chloro-1,2-benzisoxazole reacted with excess piperazine in the presence of pyridine to provide 3-(piperazin-1-yl)benzo[d]isoxazole (3A) in 76% yield. Reductive amination of compound (3A) with 2-carbomethoxy 2-methyl propionaldehyde gave alkylated piperazine (4A), which was purified over silica gel. Basic hydrolysis of the methyl ester of (4A) in aqueous ethanol followed by acidification gave the carboxylic acid (1) as the mono-HCl salt.

Sulfonamide compounds can be synthesized, for example, as shown in Scheme 2:

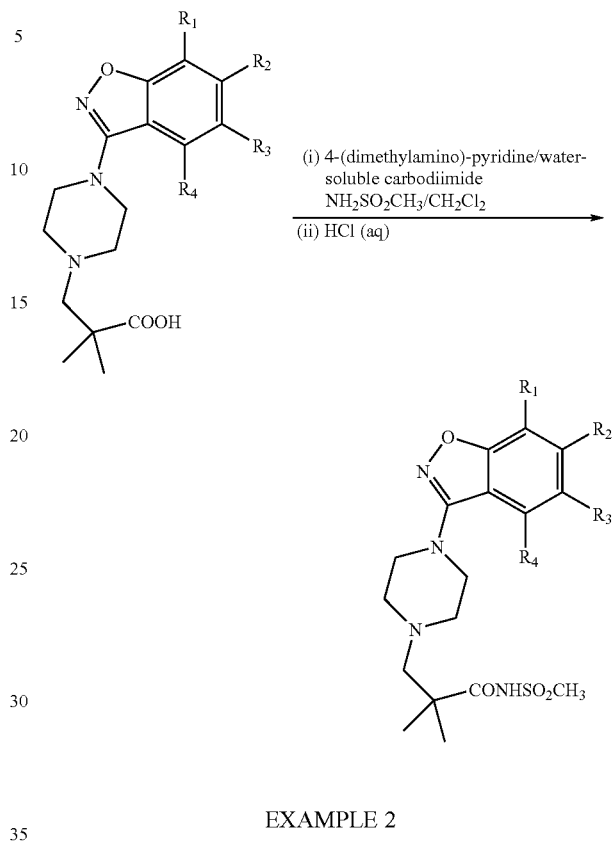

EXAMPLE 2

Evaluation of Compounds

Sleep in mammals can be divided into sleep occurring during periods of rapid eye movement (REM), accompanied by substantial brain activity, and periods of non-REM (NREM) sleep, accompanied by decreased brain activity. Typically, a normal nighttime sleep period is occupied primarily by NREM sleep, and thus NREM cumulation can serve as a measure of total sleep cumulation, e.g., significantly decreased NREM can be associated with insomnia and an accumulation of "sleep debt", e.g., an accumulated physiological need for sleep that tends to persist until a sufficient amount of additional sleep is accumulated. Thus, an increase in NREM associated with a treatment can indicated the treatment's effectiveness in treating insomnia.

Sleep quality can be associated with sleep continuity or sleep maintenance. For example, a subject with sleep apnea wakes up numerous times during a sleep period, e.g., the subject has difficulty maintaining continuous sleep. Although such a subject can accumulate a typical nights length of sleep, e.g., 8 hours, the sleep is unrefreshing due to the waking caused by the sleep apnea. Thus, an increase in the longest uninterrupted sleep bout (LUSB, also known as longest sleep bout) associated with a treatment can indicate the treatment's effectiveness in enhancing sleep continuity, and therefore in treating sleep maintenance insomnia.

Sleep-wakefulness, locomotor activity and body temperature are monitored in male Wistar rats treated with a test compound (i.e., benzisoxazole analog) initially at a concentration of 10 mg/kg. Higher and lower doses are assayed for select compounds (e.g., as high as 45 mg/kg, and as low as necessary to establish a no-effect dose). Treatments are administered at CT-18, the peak of the activity dominated period (6 hours after lights-off), and produced soporific (sleep-inducing) effects characterized by increased non-REM sleep time, increased sleep continuity, but without evidence of REM sleep inhibition or rebound insomnia.

Sleep-wakefulness, locomotor activity and body temperature were monitored in vivo with various compounds of the invention. Adult, male Wistar rats (250 g at time of surgery, Charles River Laboratories, Wilmington Mass.) were anesthetized (2% isoflourane in medical grade oxygen) and surgically prepared with a cranial implant to permit chronic electro-encephalogram (EEG) and electromyogram (EMG) recording. Body temperature and locomotor activity were monitored via a miniature transmitter (Mini-Mitter, Bend, Oreg.) surgically placed in the abdomen. The cranial implant consisted of stainless steel screws (two frontal [+3.2 AP from bregma, ±2.0 ML] and two occipital [−6.9 AP, ±5.5 ML]) for EEG recording. Two Teflon®-coated stainless steel wires were positioned under the nuchal trapezoid muscles for EMG recording. All leads were soldered to a miniature connector prior to surgery, and gas sterilized in ethylene oxide. The implant assembly was affixed to the skull with dental acrylic. A minimum of three weeks was allowed for surgical recovery.

Each rat was permanently housed in its own individual recording cage located within separate, ventilated compartments of custom-designed stainless steel cabinets. Each cage was enhanced with a filter-top riser and low-torque swivel-commutator. Food and water were available ad libitum. A 24-hr light-dark cycle (12 hours light, 12 hours dark) was maintained throughout the study. Animals were undisturbed for at least 48 hours before and after treatments.

Sleep and wakefulness were determined using "SCORE-2004™" (Hypnion, Worcester, Mass.)—an internet-based sleep-wake and physiological monitoring system. The system monitored amplified EEG (bandpass 1-30 Hz), integrated EMG (bandpass 10-100 Hz), body temperature and non-specific locomotor activity (LMA) via telemetry, and drinking activity, continuously and simultaneously. Arousal states were classified on-line as non-REM (NREM) sleep, REM sleep, wake, or theta-dominated wake every 10 seconds. Total drinking and locomotor activity counts, and body temperature were quantitiated and recorded each minute, using EEG feature extraction and pattern-matching algorithms. From this data, the longest uninterrupted sleep bout (LUSB) was obtained. The classification algorithm used individually-taught EEG-arousal-state templates, plus EMG criteria to differentiate REM sleep from theta-dominated wakefulness, plus behavior-dependent contextual rules (e.g., if the animal was drinking, it is awake). Drinking and locomotor activity intensity (LMA) were recorded every 10 seconds, while body temperature was recorded each minute. Locomotor activity was detected by a telemetry receiver (Mini-Mitter) beneath the cage. Telemetry measures (LMA and body temperature) were not part of the scoring algorithm; thus, sleep-scoring and telemetry data were independent measures.

Compounds were administered at CT-18, the peak of the activity-dominated period, sufficient time was allowed to view the time course of the treatment effect before lights-on (6 hours post-treatment). Compounds were suspended in sterile 0.25% or 0.5% methylcellulose (1-2 ml/kg). Treatments were administered orally as a bolus.

A parallel group study design was employed. Vehicle controls were drawn from a large pool (N>200): a subset of the pooled vehicle controls was selected, based on computerized matching with the 24-hour pre-treatment baseline of the active treatment group.

The following pharmacokinetic parameters are computed from the individual plasma concentrations of the modified benzisoxazole compound using a noncompartmental approach and appropriate validated pharmacokinetic software (e.g., WinNonlin Professional). Concentration values reported as BLQ are set to zero. If concentration data are available, interim calculations are done (non-QC.d data) between periods if possible. Dose escalation does not depend on pharmacokinetic calculations.

Descriptive statistics, including mean, standard deviation, coefficient of variation, geometric mean, median, minimum and maximum are computed for each pharmacokinetic parameter by dose group. Descriptive statistics for natural-log transformed AUC(0-t), AUC(0-inf), and Cmax are provided for each dose level. In addition, mean and median concentration versus time graphs are provided.

Dose proportionality following study medication is explored by analyzing natural log-transformed pharmacokinetic variables AUC(0-t), AUC(0-inf), and Cmax with a linear model including the natural log-transformed dose as covariates. Dose proportionality is concluded if the 95% confidence interval for the slope of the covariate includes the value of 1. Dose linearity for AUC(0-t), AUC(0-inf), and Cmax is also explored by a linear model. See, e.g., Gibaldi and Perrier, *Pharmacokinetics*, Second Ed., Marcel Dekker: New York, N.Y. (1982). Nominal sample collection times were used in calculations, except where actual sampling times fell outside the protocol-specified acceptable time ranges. The following parameters are estimated:

$C_{max}$ Maximum plasma concentration.

$T_{max}$ Time to maximum concentration.

$C_{max}$ and $T_{max}$ were reported directly from the concentration-time data.

$AUC_{0-t}$ Area under the plasma concentration-time curve from time 9 to the last time point with measurable concentrations, estimated by linear trapezoidal rule.

$AUC_{0-\infty}$ Area under the plasma concentration-time curve extrapolated to infinity, calculated using the formula:

$$AUC_{0-\infty} = AUC_{0-t} + C_0/\lambda_0$$

Where $C_t$ is the last measurable concentration in plasma and $\lambda_z$ is the terminal phase elimination rate constant estimated using log-linear regression during the terminal elimination phase. The number of points used in $\lambda_z$ calculation was determined by visual inspection of the data describing the terminal phase. At lest the last three time points with measurable values were used in $\lambda_z$ calculation. The number of points used in $\lambda_z$ calculation is based on the best correlation ($r_2$ adjusted) obtained for the time points describing the terminal elimination phase. A $r_2$ adjusted value for the regression line is considered to accurately define the terminal elimination phase if the value is >0.7.

$T_{1/2}$ Elimination half-life, determined by $\ln(2)\lambda_z$.

CL Systemic clearance; for intravenous bolus or infusion, calculated using the formula:

$$CL = Dose/AUC_{0-\infty}$$

Report CL/F, where F=Absolute bioavailability, for all other routes of administration.

$V_2$ Volume of distribution for all routes of administration, calculated using the formula:

$$V_z = CL\lambda_z$$

CL/F is used to calculate $V_2/F$ for extravascular routes of administration.

Pharmacokinetic analysis is performed using WinNonlin Professional Edition (Pharsight Corporation, Version 3.3 or 4.1). Descriptive statistics such as mean and standard deviation are calculated in Microsoft Excel (Version 8.0e).

Metabolism of test articles in monkey and human cryopreserved hepatocytes is assayed as follows:

| MATERIALS | |
|---|---|
| Materials | Manufacturer, lot number and exp. Date |
| Hepatocytes from Cellzdirect | Monkey Human |
| Williams E medium | Sigma W1878, exp 2004-11 |
| Foetal calf serum | Fisher BW 14-501F, lot 01104637, exp 17 Feb 10 |
| 0.45 Trypan Blue | Biowhittaker 17-942E, lot 01104637, exp January 2014 |
| Test Material Stock Solution | CB-1/III/6 |
| DMSO | Fisher BP231-100, lot 041215, exp 12 Jul 09 |
| 10 mM ethoxycoumarin in methanol | PSLB 22-A-15, exp Sep. 25, 2004 |
| ACN | Fisher A998-4, lot 041181, exp June 2007 |
| Formic Acid | Fisher 032879, exp Mar. 14, 2006 |

Pre-Incubation Preparation:

Sample is diluted with DMSO, to prepare 100 µM and 10 µM stocks. 0.1% formic acid in acetonitrile is prepared by the addition of 1 mL formic acid per 1 L acetonitrile (store RT for 3 months). 10 minute, 60 and 120 minute 96 well quenching plates are prepared with 150 µL acetonitrile+0.1% formic acid in each well. Store on ice or refrigerated.

Next, hepatocytes are thawed and 100 µL of cell suspension is placed into a microfuge tube with 100 µL 0.4% Trypan Blue solution and gently mix by inversion. A small amount of the stained cell suspension (approximately 15 µL) is placed into a clean hemacytometer with a coverslip. The hemacytometer is placed onto the stage of the microscope and the focus and power are adjusted until a single counting square fills the field. The number of cells in the four outside corner subdivided squares of the hemacytometer are counted. Viable cells are opalescent, round, and pale with a darker outline. Non-viable cells are dark, opaque blue.

The % viability is calculated as the number of viable cells divided by the total of cells ×100.

The viable cell density and total number of viable cells are calculated:

Viable cell Density (D)=Mean 3 of viable cells counted (C)×$10^4$×f2; Total number of viable cells (E)=D×26 (resuspension volume). The additional media required to achieve a concentration of $1×10^6$ cells/mL is calculated:

$$\text{Volume of additional medium} = \frac{\text{total viable cells}}{1×10^6}(E) - 26 \text{ mL}$$

Cells are diluted accordingly and stored at room temperature.

Incubations

198 µL of hepatocytes are transferred to relevant wells on dosing plate. The remaining hepatocyte suspension is combined and place in a suitable container of near boiling water and left for 5 minutes to inactivate the cells (for inactive controls and standard curve preparation).

198 µL of inactive hepatocytes are transferred to control wells and 198 µL of blank media are transferred to buffer control wells. Plates are preincubated for at least 15 min. Reactions are started 2 µL of appropriate test compound dilution from dosing plate. Plates are incubated in an incubator set at 37° C. for approximately 10 minutes, then 50 µL of incubate is removed to 10 a minute quenching plate containing 150 µL acetonitrile+0.1% formic acid and stored refrigerated or on ice. Following 60 minutes, 50 µL of incubate is removed to 60 minute quenching plate containing 150 µL acetonitrile+0.1% formic acid and stored refrigerated or on ice. Following 120 minutes, 50 µL of incubate is removed to 120 minute quenching plate containing 150 µL acetonitrile+ 0.1% formic acid and stored refrigerated or on ice. The remaining 50 µL is frozen in incubation plates. Tubes are then centrifuged at ~4° C. at ~1400×g for ~10 minutes. 100 µL of supernatant is diluted with 100 µL water in analysis plates, plates are stored frozen at −20° C. prior to analysis.

Preparation of Standard Curves 0.1 µM standard is prepared by the addition of 2 µL of 10 µM dosing solutions to 198 µL of inactive hepatocytes in standard prep plate. 150 µL acetonitrile+0.1% formic acid is added to the standard quenching plate. 150 µL of 0.1 µM standard is transferred into one column of a standard plate. 75 µL inactive hepatocytes is added to remaining wells. 75 µL from 0.1 µM standard is transferred into adjacent well in column in the plate, and mixed well by titration. Serial dilution is continued. 75 µL is removed from final standard (all wells contain 75 µL). Plates are incubated at approximately 37° C. for 10 minutes. 50 µL is transferred into standard quench plate containing 150 µL acetonitrile+0.1% formic acid. Plates are centrifuged along with samples and dilute supernatant 1:1 with water as above. Samples are stored frozen at ~−20° C.

Sleep parameters for representative compounds are shown below.

| Cmpd No | R4 | R5 | X | R0 | LONGEST UNINTERRUPTED SLEEP BOUT | | | | | MAXIMUM NREM SLEEP CUMULATION | | | | |
|---|---|---|---|---|---|---|---|---|---|---|---|---|---|---|
| | | | | | 0.3 mg/kg | 1 mg/kg | 3 mg/kg | 10 mg/kg | 30 mg/kg | 0.3 mg/kg | 1 mg/kg | 3 mg/kg | 10 mg/kg | 30 mg/kg |
| 1 | — | — | N | 2C-GDM COOH | 6.0 ± 1.7 | 9.3 ± 1.9 | 14.4 ± 3.9 | 16.2 ± 3.0 | | 20 ± 7 | 16 ± 4 | 26 ± 4 | 50 ± 7 | |
| 3 | — | — | N | 2C-GDM MSUL COOH | | | 5.2 ± 1.9 | 12.3 ± 4.2 | | | | 25 ± 6 | 27 ± 5 | |
| 4 | — | — | N | 2C COOH | | | 9.9 ± 2.2 | | | | | 27 ± 5 | | |
| 5 | — | — | N | CP-2C COOH | | 3.0 ± 1.2 | 5.1 ± 1.4 | 7.2 ± 1.5 | | | 40 ± 6 | 37 ± 8 | 45 ± 9 | |
| 6 | — | F | N | 2C- | | | 9.8 ± | 13.5 ± | | | | 18 ± | 26 ± | |

-continued

| | | | | | | | | | |
|---|---|---|---|---|---|---|---|---|---|
| | | | GDM COOH | | 2.9 | 4.0 | | 5 | 7 |
| 7 | — | OCH$_3$ | N | 2C-GDM COOH | | -2.5 ± 3.1 | | | 6 ± 4 |
| 8 | — | CH$_3$ | N | 2C-GDM COOH | 4.8 ± 2.3 | 8.6 ± 2.2 | 14.3 ± 3.6 | 15 ± 4 | 29 ± 5 | 37 ± 6 |
| 9 | CH$_3$ | — | N | 2C-GDM COOH | 13.6 ± 4.2 | 12.9 ± 3.5 | | 24 ± 5 | 29 ± 8 |
| 10 | — | — | N | 3C COOH | | 10.7 ± 1.9 | 9.9 ± 3.7 | | 22 ± 5 | 24 ± 4 |
| 11 | — | CH$_3$ | N | CP-2C COOH | | | | | |
| 12 | — | CH$_3$ | N | 2C COOH | | 7.3 ± 3.4 | | | 16 ± 4 |
| 13 | — | CH$_3$ | N | 3C COOH | | -5.6 ± 2.4 | | | 7 ± 5 |

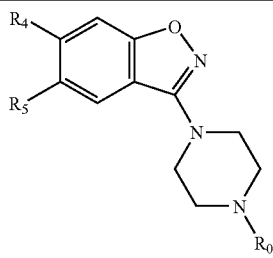

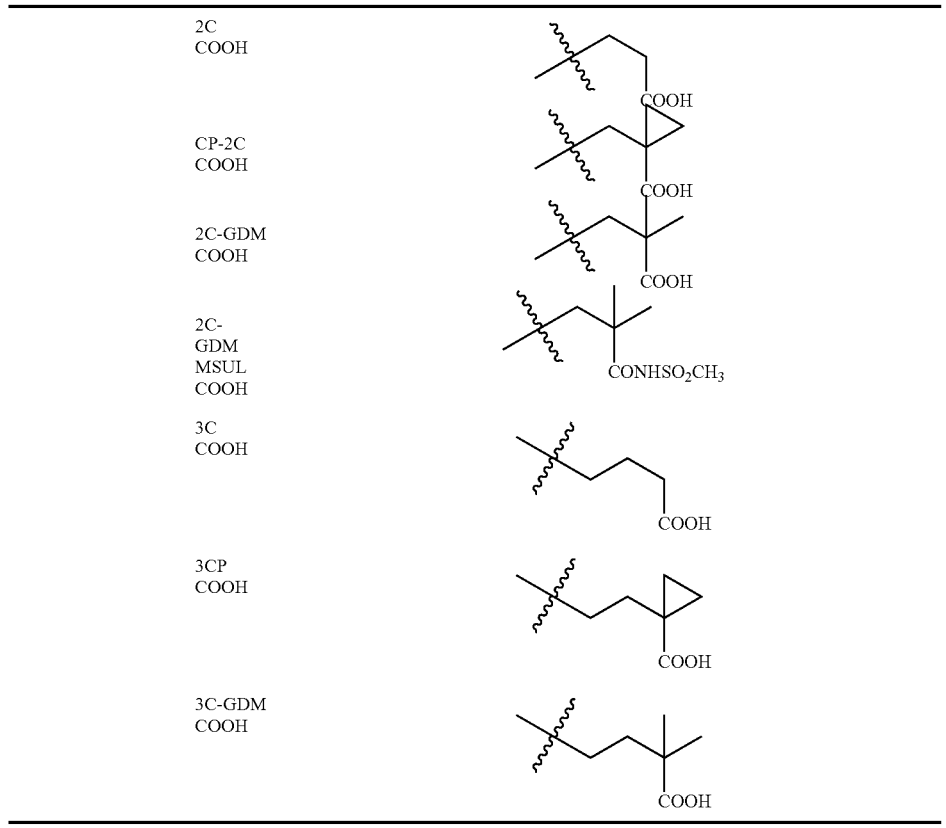

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims

We claim:

1. A compound having the formula of Compound 1:

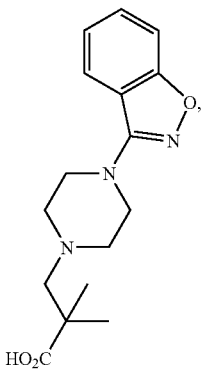

(1), or a pharmaceutically acceptable salt thereof.

2. A pharmaceutical composition comprising the compound, or pharmaceutically acceptable salt thereof, of claim 1 and at least one pharmaceutically acceptable excipient.

3. A method of treatment of insomnia in a subject, comprising administering to a subject in need of thereof a therapeutically effective amount of a composition of claim 2.

4. The method of claim 3, wherein the subject is a human.

5. The salt of claim 1 which is the monohydrochloride salt.

6. The composition of claim 2 in which the pharmaceutically acceptable salt is the monohydochloride salt.

* * * * *